United States Patent
Salama et al.

(10) Patent No.: US 12,162,868 B2
(45) Date of Patent: Dec. 10, 2024

(54) PIPERAZINE DERIVATIVES, PHARMACEUTICAL COMPOSITIONS AND METHODS OF USE THEREOF

(71) Applicant: Vidac Pharma Ltd., Ness Ziona (IL)

(72) Inventors: Paul Salama, Ashdod (IL); Vered Behar, Bet Zayit (IL); Oren Menahem Becker, Mevasseret Zion (IL)

(73) Assignee: Vidac Pharma Ltd.., Rehovot (IL)

( * ) Notice: Subject to any disclaimer, the term of this patent is extended or adjusted under 35 U.S.C. 154(b) by 396 days.

(21) Appl. No.: 17/396,707

(22) Filed: Aug. 8, 2021

(65) Prior Publication Data

US 2022/0098179 A1    Mar. 31, 2022

Related U.S. Application Data

(63) Continuation of application No. 15/735,183, filed as application No. PCT/IL2017/050909 on Aug. 17, 2017, now Pat. No. 11,084,807.

(60) Provisional application No. 62/376,396, filed on Aug. 18, 2016.

(51) Int. Cl.
| | |
|---|---|
| A61K 31/538 | (2006.01) |
| A61K 9/00 | (2006.01) |
| A61P 35/00 | (2006.01) |
| C07D 409/06 | (2006.01) |
| C07D 413/06 | (2006.01) |

(52) U.S. Cl.
CPC .......... *C07D 413/06* (2013.01); *A61K 9/0019* (2013.01); *A61P 35/00* (2018.01); *C07D 409/06* (2013.01)

(58) Field of Classification Search
CPC .............. A61K 31/538; A61K 31/4535; A61K 31/496; A61K 31/498; C07D 413/06; C07D 403/06; C07D 409/06
USPC ....... 514/229.8, 255.05, 324, 202, 102, 348, 514/375; 546/202
See application file for complete search history.

(56) References Cited

U.S. PATENT DOCUMENTS

| | | |
|---|---|---|
| 2,643,255 A | 6/1953 | Jacob et al. |
| 2,742,472 A | 4/1956 | Baltzly et al. |
| 2,838,509 A | 6/1958 | Cusic et al. |
| 2,865,930 A | 12/1958 | Arpajon et al. |
| 2,887,481 A | 5/1959 | Sherlock et al. |
| 3,284,449 A | 11/1966 | Cusic et al. |
| 3,526,630 A | 9/1970 | Toldy et al. |
| 3,585,171 A | 6/1971 | Steinhofer et al. |
| 3,700,658 A | 10/1972 | Steinhofer et al. |
| 3,803,141 A | 4/1974 | De Wall |
| 3,838,118 A | 9/1974 | Janssen et al. |
| 4,080,360 A | 3/1978 | Schlichting et al. |
| 4,188,485 A | 2/1980 | Kukla |
| 4,812,462 A | 3/1989 | Blankley et al. |
| 5,223,508 A | 6/1993 | Izawa et al. |
| 5,532,266 A | 7/1996 | Gottschlich et al. |
| 5,563,017 A | 10/1996 | Yabuki et al. |
| 5,563,165 A | 10/1996 | Talley et al. |
| 5,599,815 A | 2/1997 | Fukuda et al. |
| 5,622,953 A | 4/1997 | Janssen et al. |
| 5,760,068 A | 6/1998 | Talley et al. |
| 5,795,894 A | 8/1998 | Shue et al. |
| 5,861,394 A | 1/1999 | Urbahns et al. |
| 6,071,901 A | 6/2000 | Dorwald et al. |
| 6,235,730 B1 | 5/2001 | Sato et al. |
| 6,436,972 B1 | 8/2002 | Darvesh et al. |
| 6,462,198 B1 | 10/2002 | Bleicher et al. |
| 6,800,619 B2 | 10/2004 | Charrier et al. |
| 6,977,263 B2 | 12/2005 | Astles et al. |
| 7,119,091 B2 | 10/2006 | Habashita et al. |
| 7,161,003 B1 | 1/2007 | Guzi et al. |
| 7,196,078 B2 | 3/2007 | Guzi et al. |
| 7,531,570 B2 | 5/2009 | Randle |
| 7,592,348 B2 | 9/2009 | Zhu et al. |
| 7,615,550 B2 | 11/2009 | Heightman et al. |
| 7,635,698 B2 | 12/2009 | Rosse et al. |
| 7,700,603 B2 | 4/2010 | Zhu et al. |
| 7,759,336 B2 | 7/2010 | Habashita et al. |
| 7,763,609 B2 | 7/2010 | Zhu et al. |
| 7,919,508 B2 | 4/2011 | Shutske et al. |
| 7,960,398 B2 | 6/2011 | Miller |
| 8,017,617 B2 | 9/2011 | Ji et al. |
| 8,158,792 B2 | 4/2012 | Costanzo et al. |

(Continued)

FOREIGN PATENT DOCUMENTS

| | | |
|---|---|---|
| BE | 486462 | 4/1949 |
| CA | 946401 | 4/1974 |

(Continued)

OTHER PUBLICATIONS

Abuhaie et al. "Synthesis and anticancer activity of analogues of phenstatin, with a phenothiazine A-ring, as a new class of microtubule-targeting agents." *Bioorganic & medicinal chemistry letters* 23.1 (2013): 147-152.

Acton et al. "Some Nitrogen-Containing Ferrocene Derivatives." *The Journal of Organic Chemistry* 24.10 (1959): 1487-1490.

Adibekian et al. "Click-generated triazole ureas as ultrapotent in vivo-active serine hydrolase inhibitors." *Nature chemical biology* 7.7 (2011): 469-478.

Bâcu et al. "Synthesis of pyrrolo[1,2-b]pyridazine-phenothiazine hybrid compounds", Departement de Chimie. Organique et Biochimie, Faculte de Chimie, Universitatea "Al. I. Cuza", Iasi, RO-6600, Rom., COFrRoCA 2002, *Actes du Colloque Franco-Roumain de Chimie Appliquee*, 2nd, Bacau, Romania, Oct. 10-12, 2002 (2002), 91-92.

(Continued)

*Primary Examiner* — Jeffrey H Murray
(74) *Attorney, Agent, or Firm* — Mark S. Cohen; PEARL COHEN ZEDEK LATZER BARATZ LLP

(57) ABSTRACT

The present invention relates to novel piperazine derivatives, methods for their preparation, pharmaceutical compositions including such compounds, and methods of using these compounds and compositions, especially for targeted therapy treatment of hyperproliferative disorders, including benign hyperproliferative disorders, cancer and pre-cancer conditions.

31 Claims, No Drawings

(56) References Cited

U.S. PATENT DOCUMENTS

| | | |
|---|---|---|
| 8,202,891 B2 | 6/2012 | Husfeld et al. |
| 8,580,782 B2 | 11/2013 | Guzi et al. |
| 8,642,660 B2 | 2/2014 | Goldfarb |
| 8,673,924 B2 | 3/2014 | Guzi et al. |
| 8,765,667 B2 | 7/2014 | Eissenstat et al. |
| 8,772,307 B2 | 7/2014 | Frank et al. |
| 9,016,221 B2 | 4/2015 | Brennan et al. |
| 9,203,080 B2 | 12/2015 | Deronzier et al. |
| 9,206,173 B2 | 12/2015 | Takahashi et al. |
| 9,326,973 B2 | 5/2016 | Hewawasam et al. |
| 9,346,769 B2 | 5/2016 | Bahadoor et al. |
| 11,084,807 B2 * | 8/2021 | Salama ............ C07D 409/06 |
| 11,266,639 B2 * | 3/2022 | Behar ............. A61K 51/0491 |
| 2003/0013712 A1 | 1/2003 | Tullis et al. |
| 2004/0097734 A1 | 5/2004 | Gerlach et al. |
| 2004/0147502 A1 | 7/2004 | Bisacchi et al. |
| 2007/0037752 A1 | 2/2007 | Ansorge et al. |
| 2010/0160255 A1 | 6/2010 | Kamata et al. |
| 2010/0179118 A1 | 7/2010 | Ozawa et al. |
| 2010/0248365 A1 | 9/2010 | Crawford et al. |
| 2011/0046368 A1 | 2/2011 | Vashchenko et al. |
| 2011/0178066 A1 | 7/2011 | Ohler et al. |
| 2015/0023913 A1 | 1/2015 | Hewawasam et al. |
| 2016/0058745 A1 | 3/2016 | Sheridan et al. |
| 2016/0158200 A1 | 6/2016 | Hewawasam et al. |
| 2016/0354375 A1 | 12/2016 | Sheridan et al. |
| 2018/0303819 A1 | 10/2018 | Behar et al. |
| 2018/0303820 A1 | 10/2018 | Behar et al. |
| 2020/0188381 A1 | 6/2020 | Behar et al. |

FOREIGN PATENT DOCUMENTS

| | | |
|---|---|---|
| CA | 2353369 | 7/2001 |
| CH | 333366 | 10/1958 |
| CH | 653675 | 1/1986 |
| CN | 102690717 | 9/2012 |
| CN | 103896990 | 2/2014 |
| CN | 104109133 | 10/2014 |
| CN | 104109134 | 10/2014 |
| CN | 104557875 | 4/2015 |
| CN | 104497013 | 8/2015 |
| DE | 954155 | 12/1956 |
| DE | 3607194 | 10/1987 |
| EP | 476928 | 3/1992 |
| FR | 1192168 | 10/1959 |
| FR | 1529869 | 6/1968 |
| FR | 6541 | 12/1968 |
| GB | 666457 | 2/1952 |
| GB | 748812 | 9/1956 |
| GB | 773756 | 1/1957 |
| GB | 778309 | 3/1957 |
| GB | 777209 | 6/1957 |
| GB | 781528 | 8/1957 |
| GB | 1224207 | 3/1971 |
| GB | 1276318 | 1/1972 |
| HU | 153318 | 12/1966 |
| IN | 200700871 | 6/2009 |
| JP | 53034779 | 3/1978 |
| JP | H 03251564 | 11/1991 |
| JP | 04356466 | 10/1992 |
| JP | 05273701 | 10/1993 |
| JP | 06211664 | 2/1994 |
| JP | 06228095 | 8/1994 |
| JP | 08110621 | 4/1996 |
| JP | 08217758 | 8/1998 |
| JP | 11292840 | 10/1999 |
| JP | 2002047272 | 2/2002 |
| JP | 2012111731 | 6/2012 |
| WO | WO 1997046549 | 12/1997 |
| WO | WO 2001092240 | 6/2001 |
| WO | WO 2004022561 | 3/2004 |
| WO | WO 2005058311 | 6/2005 |
| WO | WO 2006105056 | 5/2006 |
| WO | WO 2006082354 | 10/2006 |
| WO | WO 2007008541 | 1/2007 |
| WO | WO 2007076055 | 5/2007 |
| WO | WO/2007/066336 | 6/2007 |
| WO | WO 2007146122 | 12/2007 |
| WO | WO 2008009935 | 1/2008 |
| WO | WO 2008011392 | 1/2008 |
| WO | WO 2009100872 | 8/2009 |
| WO | WO 2012138877 | 11/2012 |

OTHER PUBLICATIONS

Bâcu et al. "Benzoindolizine derivatives of N-acylphenothiazine. Synthesis and characterization." *Organic & biomolecular chemistry* 1.13 (2003): 2377-2382.

Bâcu et al. "Synthese de nouveaux derives de la phenothiazine a activite pharmacologique potentielle", COFrRoCA 2004, *Actes du Colloque Franco-Roumain de Chimie Appliquee*, 2nd, Bacau, Romania, Sep. 22-26, 2004, 37-38.

Bâcu et al. "Synthesis of Pyrrolo [1, 2-b] pyridazine Derivatives Engrafted on N-Acylphenothiazine." *Revue Roumaine de Chimie* (2006) 51(9): 887-894.

Bâcu et al. "Synthesis of New N-Acylphenothiazinic Derivatives with Potential Activity in Chemotherapy." *Revue Roumaine de Chimie* (2007) 52(3): 253-259.

Baumhover "The synthesis and development of novel multicomponent polyacridine gene delivery systems" (dissertation) Doctor of Philosophy (PhD); University of Iowa; Autumn 2010.

Belei et al. "A New Synthetic Methodology for the Pyrrolidine Ring." *Synlett* Jun. 2010 (2010): 931-933.

Berenguer et al. "Anthelmintics. V. Oxyuricidal and strongylicidal activity of piperazine, phenothiazine, and some phenothiazine-piperazine derivatives", Inst. *"Lopez-Neyra" Parasitol.*, Granada, Spain, *Revista Iberica de Parasitologia* (1973), 33(1), 81-106, CODEN: RIPAAE; ISSN: 0034-9623.

Bergman et al. "The reaction of indole and the indole grignard reagent with phosgene. A facile synthesis of indole-3-carboxylic acid derivatives." *Journal of Heterocyclic Chemistry* 14.7 (1977): 1123-1134.

Biniecki et al. "Synthesis of N-(pyridinecarbonyl)phenoxazines" Akad. *Med.*, Warsaw, Pol., *Acta Poloniae Pharmaceutica* (1972), 29(6), 541-4.

Borsy et al. "Investigation of gastric ulcer inhibiting and secretoinhibitory actions of xanthene derivatives." Acta pharmaceutica Hungarica 38.2 (1968): 151-158.

Borsy et al. "2-Pyridylthioacetamide, a new antisecretory and antiulcer drug", Res. Inst. Pharm. Chem., Budapest, Hung., Congr. Hung. Pharmacol. Soc., [Proc.]. 1st (1973), Meeting Date 1971, vol. 3, 67-78.

Buchwald (1980) "Long-term, continuous intravenous heparin administration by an implantable infusion pump in ambulatory patients with recurrent venous thrombosis" *Surgery*, 88(4), 507-516.

Cahn et al. "A biochemical concept of experimental psychoses. VII. Actions of N-thiodiphenylcarbamylpiperazine (MD 5501) and chlorpromazine on the disturbances of humoral balance and cerebral metabolism provoked by chronic administration of lysergic acid diethylamide to rabbits", Hop. Pitie, Paris, *Comptes Rendus des Seances de la Societe de Biologie et de Ses Filiales*, (1958), 152, 483-5.

Carafa et al. "A simple direct phosgeneless route to N-heteroaryl unsymmetrical ureas." Green chemistry 14.1 (2012): 217-225.

CAS Registry No. 1026968-94-4; CA Index Name: Methanone, [4-(3,5-dimethoxyphenyl)-1-piperazinyl]-9H-fluoren-9-yl-. STN Entry Date Jun. 10, 2008.

CAS Registry No. 432497-13-7; CA Index Name: 1-Piperazinecarboxylic acid, 4-(10H-phenothiazin-10-ylcarbonyl)-, ethyl ester. STN Entry Date Jun. 20, 2002.

CAS Registry No. 432528-56-8; CA Index Name: Methanone, [4-(4-nitrophenyl)-1-piperazinyl]-10H-phenothiazin-10-yl-. STN Entry Date Jun. 20, 2002.

CAS Registry No. 433947-75-2; CA Index Name: Methanone, [4-(4-fluorophenyl)-1-piperazinyl]-10H-phenothiazin-10-yl-. STN Entry Date Jun. 26, 2002.

(56) References Cited

OTHER PUBLICATIONS

CAS Registry No. 852704-21-3; CA Index Name: Methanone, 9H-fluoren-9-yl(4-phenyl-1-piperazinyl)-. STN Entry Date Jun. 22, 2005.
CAS Registry No. 873579-51-2; CA Index Name: 10H-Phenothiazine, 10-[[4-(5-chloro-2-methylphenyl)-1-piperazinyl]carbonyl]-. STN Entry Date Feb. 6, 2006.
CAS Registry No. 927053-66-5; CA Index Name: Methanone, 9H-fluoren-9-yl[4-(2-pyridinyl)-1-piperazinyl]-. STN Entry Date Mar. 18, 2007.
CAS Registry No. 927070-82-4; CA Index Name: Methanone, 9H-fluoren-9-yl[4-(4-nitrophenyl)-1-piperazinyl]-. STN Entry Date Mar. 18, 2007.
CAS Registry No. 927077-37-0; CA Index Name: Methanone, 9H-fluoren-9-yl[4-(2-pyrimidinyl)-1-piperazinyl]-. STN Entry Date Mar. 18, 2007.
CAS Registry No. 927604-97-5; CA Index Name: 1-Piperazinecarboxylic acid, 4-(9H-fluoren-9-ylcarbonyl)-, 1,1-dimethylethyl ester. STN Entry Date Mar. 20, 2007.
Chen et al. "An efficient reduction of N-substituted carbonylimidazolides into formamides by NaBH4." Tetrahedron Letters 58.22 (2017): 2166-2170.
Collino et al. "Mannich bases of benzimidazoles, benzotriazoles and analogs with pharmacological activity II" Bollettino chimico farmaceutico. May 1982;121(5):221-9.
Copisarow, Maurice "N-Acyl derivatives of carbazole", Univ. Manchester, Journal of the Chemical Society, Transactions (1918), 113, 816-20.
Dahlbom "Basically Substituted Derivatives of Phenothiazine-10-carboxylic Acid" Acta Chemica Scandinavica (1953) 7: 879-84.
Darvesh et al. "Differential binding of phenothiazine urea derivatives to wild-type human cholinesterases and butyrylcholinesterase mutants." Bioorganic & medicinal chemistry 18.6 (2010): 2232-2244.
Darvesh et al. "Selective reversible inhibition of human butyrylcholinesterase by aryl amide derivatives of phenothiazine." Bioorganic & medicinal chemistry 15.19 (2007): 6367-6378.
Elben et al. "Crown ethers with different pharmacophore groups" Chemischer Informationsdienst 10.50 (1979).
El-Said, M. K. "Synthesis of New Phenothiazine Derivatives as Potential Tranquilizers and Sedatives" Chemischer Informationsdienst 13.7 (1982).
Fadda et al. "Synthesis, antimicrobial evaluation and molecular modeling of some novel phenothiazine derivatives." RSC advances 5.98 (2015): 80844-80852.
Falkenstein et al. "Disubstituted carbamoyl lactams and n-carboxylic esters of lactans as activators for anionic polymerization of lactams." Makromolekulare Chemie 127.Sep. 1969: 34-+.
Feng et al. "Structure-activity analysis of a novel NR2C/NR2D-preferring NMDA receptor antagonist: 1-(phenanthrene-2-carbonyl) piperazine-2, 3-dicarboxylic acid." British journal of pharmacology 141.3 (2004): 508-516.
Gerlach et al. "Design and Synthesis of a Focused Library of Novel Aryl- and Heteroaryl-Ketopiperazides." Archiv der Pharmazie: An International Journal Pharmaceutical and Medicinal Chemistry 337.12 (2004): 695-703.
Ghinet et al. "Studies on pyrrolidinones. Reaction of pyroglutamic acid and vinylogues with aromatics in Eaton's reagent." Tetrahedron 68.4 (2012): 1109-1116.
Goldberg et al. "Spasmolytics derived from xanthene. II", Anglo Estate, Somerset, UK, Journal of the Chemical Society (1960) 453-5.
Guo et al. "Novel photoinduced electron transfer reaction of N-methylphenothiazine in carbon tetrachloride." Chinese Chemical Letters (1998) 9(3):237-240.
Guo et al. "A novel photoinduced electron transfer reaction of N-alkylphenothiazines in carbon tetrachloride." Science in China Series B: Chemistry 42.2 (1999): 170-177.

Hallberg et al. "An intramolecular anionic fries rearrangement of N-acylphenothiazines" Tetrahedron letters 27.18 (1986): 1959-1962.
Hernandez-Olmos et al. "N-substituted phenoxazine and acridone derivatives: structure-activity relationships of potent P2X4 receptor antagonists." Journal of medicinal chemistry 55.22 (2012): 9576-9588.
Hromatka et al. "Phenothiazine derivatives. V. Piperazine and acid amide-like substituted piperazine derivatives of phenothiazine", Univ. Vienna, Monatshefte fuer Chemie (1957), 88, 242-9 CODEN: MOCMB7; ISSN: 0026-9247.
Ishigaki et al. "Hysteretic Tricolor Electrochromic Systems Based on the Dynamic Redox Properties of Unsymmetrically Substituted Dihydrophenanthrenes and Biphenyl-2, 2'-Diyl Dications: Efficient Precursor Synthesis by a Flow Microreactor Method." Materials 4.11 (2011): 1906-1926.
Khromov-Borisov et al. "Synthesis of some acyl derivatives of phenothiazine. III. Derivatives of nicotinic acid", 1st Med. Inst., Leningrad, Zhurnal Obshchei Khimii (1960), 30, 3569-72.
Kolho et al. (1993) "Hepatitis C antibodies in dialysis patients and patients with leukemia"—Journal of medical virology, 40(4), 318-321.
Kukla et al. "Use of the butaclamol template in a search for antipsychotic agents with lessened side effects." Journal of medicinal chemistry 22.4 (1979): 401-406.
Lack et al. "Targeting the binding function 3 (BF3) site of the human androgen receptor through virtual screening." Journal of medicinal chemistry 54.24 (2011): 8563-8573.
Lambrou Demetrios "Synthesis and pharmacological study of (nor-meperidine carbonyl)-10-phenothiazines ", Lab. Pharm. Chim., Univ. Athenes, Athens, 144, Greece, Pharmakeutikon Deltion, Epistemonike Ekdosis (1978), 4(1), 1-6.
Light et al. "Antiacetylcholine activity of piperazine derivatives." Journal of the American Pharmaceutical Association 46.5 (1957): 279-287.
Lin, Go Mei "The filaricidal activity of diethylcarbamazine", Singapore, Singapore, Pharmaceutica (Singapore) (1979), 1978 67-8.
Liu et al. "Synthesis, crystal structure, and magnetic properties of one copper (II) complex based on mixed xanthene-9-carboxylate and 2, 2'-bipyridine ligands." Synthesis and Reactivity in Inorganic, Metal-Organic, and Nano-Metal Chemistry 40.8 (2010): 503-509.
Lu et al. "Synthesis of N-Acylcarbazoles through Palladium-Catalyzed Aryne Annulation of 2-Haloacetanilides." The Journal of organic chemistry 77.24 (2012): 11153-11160.
Lukevics et al. "Synthesis and neurotropic properties of N-acylphenothiazines." Chemistry of Heterocyclic Compounds 33.2 (1997): 229-233.
Makhaeva et al. "Conjugates of γ-Carbolines and Phenothiazine as new selective inhibitors of butyrylcholinesterase and blockers of NMDA receptors for Alzheimer Disease" Sci Rep. 2015;5:13164.
Markgraf et al. "A versatile route to benzocanthinones." Tetrahedron 61.38 (2005): 9102-9110.
Morren et al. "The filaricidal derivatives of 1-methylpiperazine", Union chim. Belge, Brussels, Bulletin des Societes Chimiques Belges (1950), 59, 228-37.
Nagel et al. "Pharmacologic inhibition of MALT1 protease by phenothiazines as a therapeutic approach for the treatment of aggressive ABC-DLBCL." Cancer cell 22.6 (2012): 825-837.
Olah "Synthesis and investigation of organic fluorine compounds. XXV. The preparation of alkyl fluoroformates and remarks relative to a new published preparation of alkyl fluorides" Journal of Organic Chemistry (1956) 21:1319-20.
Podolesov B. D. "Oxidation of 10-acylphenothiazine derivatives with phenyllodosoacetate", Chem. Fac., Univ. Skopje, Skopje, Yugoslavia, Prilozi—Makedonska Akademija na Naukite i Umetnostite, Oddelenie za Prirodo-Matematicki Nauki (1978), 10(1), 49-52.
Podolesov et al. "Preparation of some 10-acylphenothiazine 5-oxides" Prirodnomat. Fak., Univ. Skopje, Skopje, Yugoslavia, Godisen Zbornik—Prirodno-Matematicki Fakultet na Univerzitetot Kiril i Metodij-Skopje, Sekcija A: Matematika, Fizika i Hemija (1971), 21, 39-42.
Podolesov et al. "Preparation of some 10-aroylphenothiazine derivatives", Hem. Inst., Prirodnomat. Fak., Skopje, Yugoslavia, Godisen

(56) References Cited

OTHER PUBLICATIONS

*Zbornik—Prirodno-Matematicki Fakultet na Univerzitetot Kiril i Metodij-Skopje, Sekcija A: Matematika, Fizika i Hemija* (1969), 19, 91-3.
Pollard et al. "Derivatives of piperazine. XXXIV. Some reactions of trimethylene chlorobromide with 1-arylpiperazines" The Journal of Organic Chemistry. Jun. 1959;24(6):764-7.
Prewysz-Kwinto A. "Synthesis of 2-carbethoxybenzofurans", *Inst. Org. Chem.*, Torun, Pol., *Khimiya Geterotsiklicheskikh Soedinenil* (1987), (6), 756-9.
Prinz et al. "N-heterocyclic (4-phenylpiperazin-1-yl) methanones derived from phenoxazine and phenothiazine as highly potent inhibitors of tubulin polymerization" *Journal of medicinal chemistry* 60.2 (2017): 749-766.
Rochlin et al. "Stable simple enols. 31. Substituted xanthenylidene enols. The importance of beta.-Ar—C: C conjugation in the stabilization of aryl-substituted enols." *Journal of the American Chemical Society* 114.1 (1992): 230-241.
Rogers-Evans et al. "Identification of novel cannabinoid receptor ligands via evolutionary de novo design and rapid parallel synthesis." *QSAR & Combinatorial Science* 23.6 (2004): 426-430.
Samolovova et al. "Phenoxazine series. VI. Synthesis of some 10-substituted phenoxazines." *Zh. Obshch. Khim* 32 (1962): 1085-1088.
Sandberg, F. "Phytochemical studies on the flora of Egypt. I. The alkaloids of Retama raetam Webb & Berth." *Svensk farmaceutisk tidskrift* 61.13 (1957): 345.
Saudek et al. (1989) "A preliminary trial of the programmable implantable medication system for insulin delivery"—*New England Journal of Medicine*, 321(9), 574-579.
Schreibman et al. "Synthesis of Some Amides and Amines Containing the 1, 4-Benzodioxan Nucleus as Potential Adrenolytic Agents" *Journal of Pharmaceutical Sciences* 53.8 (1964): 985-986.
Shinde et al. "Synthesis of spiro [chroman-2, 4'-piperidin]-4-one derivatives as acetyl-CoA carboxylase inhibitors." *Bioorganic & medicinal chemistry letters* 19.3 (2009): 949-953.
Suzuki et al. "Structure-activity relationship of newly synthesized quinoline derivatives for reversal of multidrug resistance in cancer." *Journal of medicinal chemistry* 40.13 (1997): 2047-2052.
Taffs LF. "Pinworm infections in laboratory rodents: a review" *Lab Anim.* 1976;10(1):1-13.
Takamatsu et al. "Synthesis of Carbazoles by Copper-Catalyzed Intramolecular C—H/N—H Coupling." *Organic letters* 16.11 (2014): 2892-2895.
Ting, A. et al. (1978) "Reactivity of autolymphocytotoxic antibodies from dialysis patients with lymphocytes from chronic lymphocytic leukemia CLL) patients"—*Transplantation*, 25(1), 31-33.
Toldy et al. "Xanthene derivatives with antiulcerogenic effects", Inst. Arzneimittelforsch., Budapest, Hung., *Conf. Hung. Ther. Invest. Pharmacol., Soc. Pharmacol. Hung.*, 4th (1968), Meeting Date 1966, 259-62.
Toldy et al. "Piperazine derivatives. III. Diethylcarbamyl and xanthene derivatives", Inst. Med. Res., Budapest, Hung., *Acta Chimica Academiae Scientiarum Hungaricae* (1971), 70(1-2), 101-22.
Walter et al. "Derivatives of 3-Piperidinol as Central Stimulants." *Journal of medicinal chemistry* 11.4 (1968): 792-796.
Wright et al. "Hypocholesteremic agents. IV. Substituted piperazines", Res. Div., Abbott Lab., N. Chicago, IL, USA, *Journal of Medicinal Chemistry* (1968), 11(2), 390-1.
Ying et al. "Total synthesis of (+)-antofine and (−)-cryptopleurine." *European journal of organic chemistry* 2013.15 (2013).
Ying et al. "Direct synthesis of arenecarboxamides through Friedel-Crafts acylation using ureas." *Tetrahedron letters* 55.33 (2014): 4541-4544.
Zaugg et al. "Solvolysis of xanthenyl and fluorenyl ion pairs in 1, 2-dimethoxyethane (DME)." *The Journal of Organic Chemistry* 39.6 (1974): 851-853.
Zelent et al. "Spectrochemical properties of some 1-substituted derivatives of carbazole." *Canadian journal of spectroscopy* 28.6 (1983): 188-195.
Zelent et al. "Spectrochemical properties of some 3-substituted derivatives of carbazole." *Canadian journal of spectroscopy* 29.1 (1984): 23-30.
Zelent et al. "One-electron photooxidation of carbazole in the presence of carbon tetrachloride. Part I. Carbon tetrachloride and ethanol used as reaction media" *Canadian Journal of Chemistry* 60.8 (1982): 945-956.

* cited by examiner

PIPERAZINE DERIVATIVES, PHARMACEUTICAL COMPOSITIONS AND METHODS OF USE THEREOF

FIELD OF THE INVENTION

The present invention relates to the field of piperazine derivatives, methods for their preparation, pharmaceutical compositions including such compounds, and methods of using these compounds, especially for targeted therapy of hyperproliferative disorders, including benign hyperproliferative disorders, cancers and pre-cancerous conditions.

BACKGROUND OF THE INVENTION

Despite significant developments in anti-cancer technology, cancer still remains the second leading cause of death following heart disease in the United States. Most often, cancer is treated with chemotherapeutic agents. In many cases, these chemotherapeutic agents show a dose responsive effect, and cell killing is proportional to drug dose. A highly aggressive style of dosing is thus necessary to eradicate neoplasms. However, high-dose chemotherapy is hindered by poor selectivity for cancer cells and severe toxicity to normal cells. This lack of tumor-specific treatment is one of the many hurdles that still needs to be overcome by currently available chemotherapy.

SUMMARY OF THE INVENTION

In one aspect, the present invention features a compound represented by the structure of Formula (II):

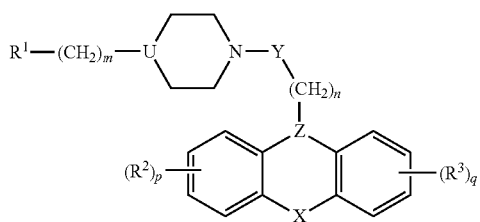

(II)

wherein
U and Z are each independently N or CH;
X is O, NH, S, or a bond;
Y is $CH_2$, C=O, or C=S;
$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$, or a combination thereof;
$R^2$ and $R^3$ are each independently at each occurrence selected from the group consisting of: halogen, $NO_2$, CN, $C_1$-$C_4$ alkyl, $OR^4$, and $NR^{5a}R^{5b}$;
$R^4$, $R^a$, $R^{5a}$, and $R^{5b}$ are each independently hydrogen or $C_1$-$C_4$ alkyl;
n is 0 or 1;
m is 0, 1, or 2;
p and q are each independently selected from 0, 1, 2, 3, and 4; and
or a pharmaceutically acceptable salt thereof;
with the proviso that:
(1) when Z is CH, X is NH, S, or a bond;
(2) the following compounds are excluded:
(i) a compound of formula (II) wherein X is NH, Z is CH, Y is C=O, n is 0, m is 0, $R^1$ is a phenyl substituted by one or more alkoxy, and p and q are each 0; and
(ii) a compound of formula (II) wherein X is S, Z is N, Y is C=O, n is 0, m is 0, $R^1$ is pyridinyl and p and q are each 0.

In another aspect, the invention relates to a pharmaceutical composition comprising a compound as described anywhere herein, or a pharmaceutically acceptable salt thereof, and a pharmaceutically acceptable carrier.

In yet another aspect, the present invention relates to a method for treating cancer, a pre-cancerous condition or a benign hyperproliferative disorder in a subject in need thereof, comprising the step of administering to the subject a therapeutically effective amount of a compound represented by the structure of Formula (II), or a pharmaceutically acceptable salt thereof:

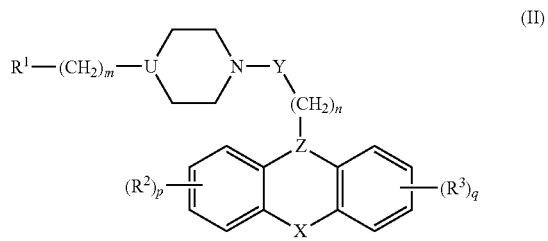

(II)

wherein
U and Z are each independently N or CH;
X is O, NH, S, or a bond;
Y is $CH_2$, C=O, or C=S;
$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$, or a combination thereof;
$R^2$ and $R^3$ are each independently at each occurrence selected from the group consisting of: halogen, $NO_2$, CN, $C_1$-$C_4$ alkyl, $OR^4$, and $NR^{5a}R^{5b}$;
$R^4$, $R^a$, $R^{5a}$, and $R^{5b}$ are each independently hydrogen or $C_1$-$C_4$ alkyl;
n is 0 or 1;
m is 0, 1, or 2; and
p and q are each independently selected from 0, 1, 2, 3, and 4;
or a pharmaceutically acceptable salt thereof,
with the proviso that:
(1) when Z is CH, X is NH, S, or a bond;
(2) the following compounds are excluded:
(i) a compound of formula (II) wherein X is NH, Z is CH, Y is C=O, n is 0, m is 0, $R^1$ is a phenyl substituted by one or more alkoxy, and p and q are each 0; and
(ii) a compound of formula (II) wherein X is S, Z is N, Y is C=O, n is 0, m is 0, $R^1$ is pyridinyl and p and q are each 0.

In some embodiments, the cancer comprises a solid tumor. In some embodiments, the solid tumor is prostate cancer, pancreatic cancer, colon cancer, cervical cancer, lung cancer, breast cancer, liver cancer, skin cancer, and melanoma, or metastases thereof. In some embodiments, the cancer comprises squamous cell carcinoma (SCC), basal cell carcinoma (BCC), cutaneous T-cell lymphoma (CTCL), or metastases thereof.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PRESENT INVENTION

In one aspect, the present invention provides a compound represented by the structure of Formula (II):

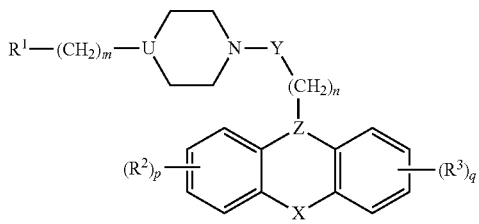

(II)

wherein
U and Z are each independently N or CH;
X is O, NH, S, or a bond;
Y is $CH_2$, C=O, or C=S;
$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$, or a combination thereof;
$R^2$ and $R^3$ are each independently at each occurrence selected from the group consisting of: halogen, $NO_2$, CN, $C_1$-$C_4$ alkyl, $OR^4$, and $NR^{5a}R^{5b}$;
$R^4$, $R^a$, $R^{5a}$, and $R^{5b}$ are each independently hydrogen or $C_1$-$C_4$ alkyl;
n is 0 or 1;
m is 0, 1, or 2;
p and q are each independently selected from 0, 1, 2, 3, and 4; and
or a pharmaceutically acceptable salt thereof, with the proviso that when Z is CH, X is NH, S, or a bond.

In another embodiment, the following compound is excluded: a compound of Formula (II) wherein X is NH, Z is CH, Y is C=O, n is 0, m is 0, $R^1$ is a phenyl substituted by one or more alkoxy, and p and q are each 0.

In some embodiments, in the compound of Formula (II), m and n are each 0.

In some embodiments, in the compound of Formula (II), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (II), p is 0. In some embodiments, q is 0. In other embodiments, p is 0 and q is 0.

In some embodiments, in the compound of Formula (II), U is N.

In some embodiments, the compound of the invention is represented by a compound of Formula (III):

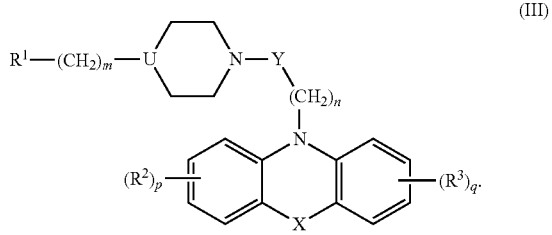

(III)

wherein X, U, $R^1$, $R^2$, $R^3$, m, n, p, and q are defined as anywhere herein.

In some embodiments, in the compound of Formula (III), X is O, NH, or a bond. In some embodiments, X is O. In other embodiments, X is a bond. In certain embodiments, X is NH.

In some embodiments, in the compound of Formula (III), m and n are each 0.

In some embodiments, in the compound of Formula (III), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (III), p is 0. In some embodiments, q is 0. In other embodiments, p is 0 and q is 0.

In some embodiments, in the compound of Formula (III), U is N.

In some embodiments, the compound of invention is represented by a compound of Formula (IV)

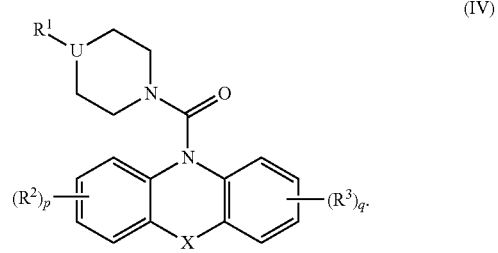

(IV)

wherein X, U, $R^1$, $R^2$, $R^3$, m, n, p, and q are defined as anywhere herein.

In some embodiments, in the compound of Formula (IV), X is O. In other embodiments, X is S. In certain embodiments, X is NH.

In some embodiments, in the compound of Formula (IV), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments, $R^2$ is H and $R^3$ is H.

In some embodiments, in the compound of Formula (IV), p is 0. In some embodiments, q is 0. In other embodiments, p is 0 and q is 0.
In some embodiments, in the compound of Formula (IV), U is N.
In some embodiments, the compound of the invention is:
(11)
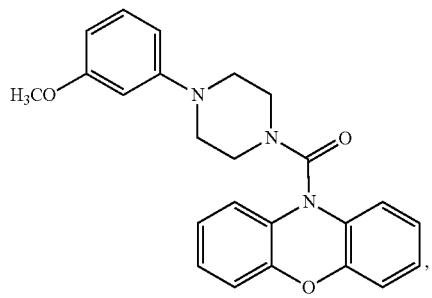
(12)
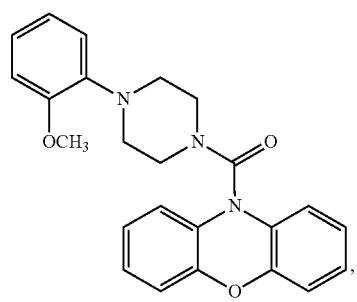
(13)
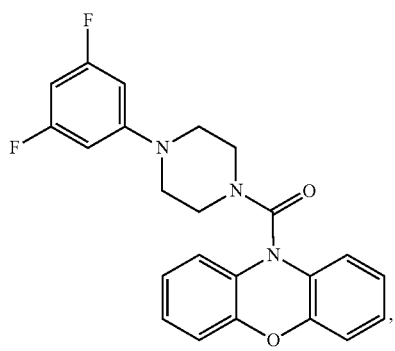
(1)
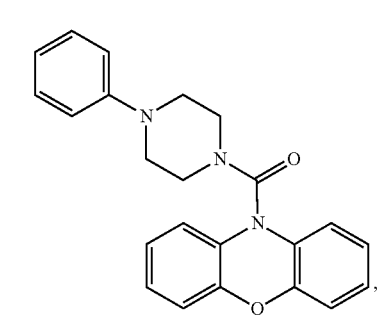
(14)
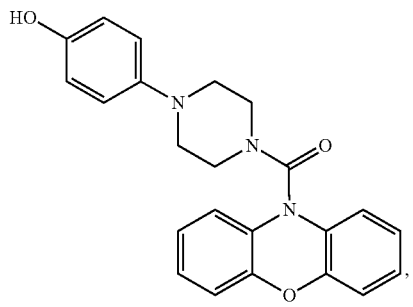
(15)
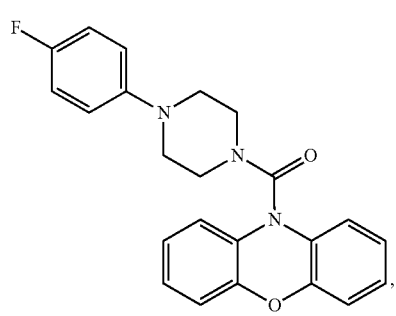
(5)
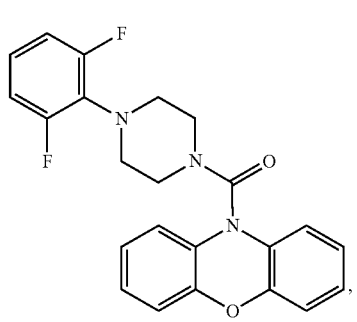
(4)
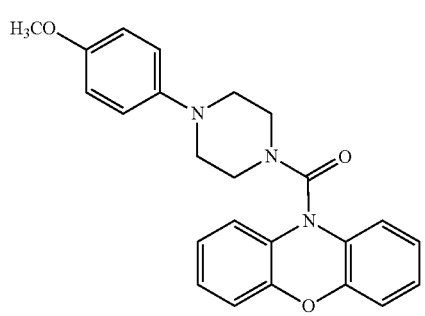
(16)
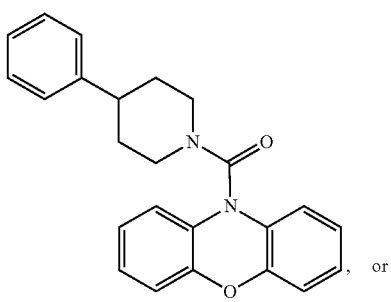, or -continued (2)
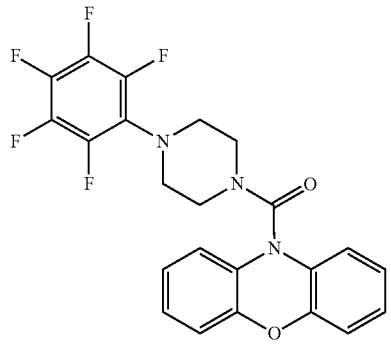

including salts, hydrates, solvates, polymorphs, optical isomers, geometrical isomers, enantiomers, diastereomers, and mixtures thereof.

In some embodiments, the compound of the invention is represented by a compound of Formula (V):

(V)
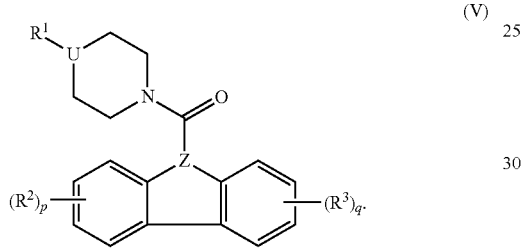

wherein X, U, $R^1$, $R^2$, $R^3$, m, n, p, and q are defined as anywhere herein.

In some embodiments, in the compound of Formula (V), Z is N. In other embodiments, Z is CH.

In some embodiments, in the compound of Formula (V), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl. In some embodiments, $R^2$ is H. In some embodiments, $R^3$ is H. In other embodiments, $R^2$ is H and $R^3$ is H.

In some embodiments, in the compound of Formula (V), p is 0. In some embodiments, q is 0. In other embodiments, p is 0 and q is 0.

In some embodiments, in the compound of Formula (V), U is N.

In some embodiments, the compound of the invention is:

(20)
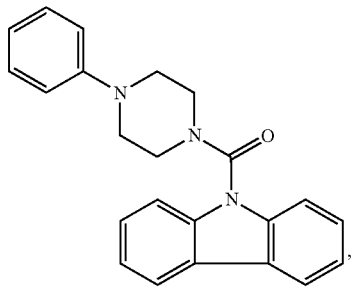

(21)
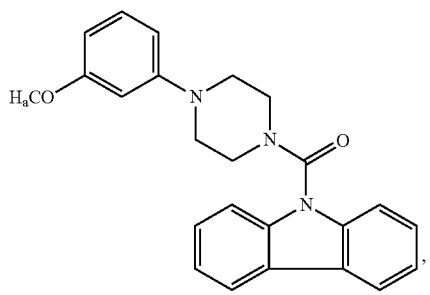

(22)
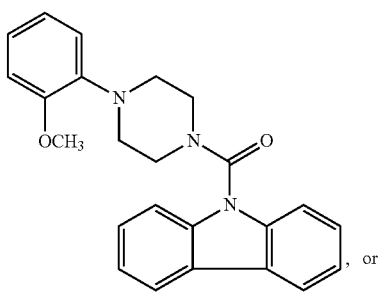
, or

(23)
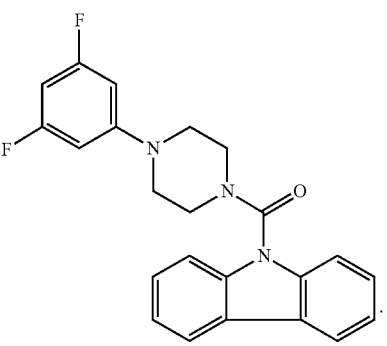

In some embodiments, the compound of the invention is represented by a compound of Formula (VI):

(VI)
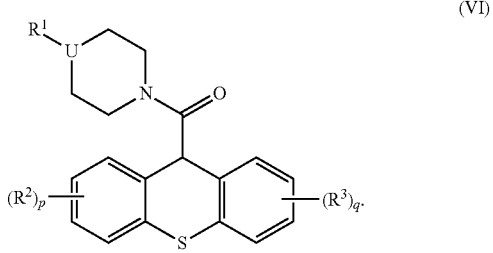

wherein U, $R^1$, $R^2$, $R^3$, p, and q are defined as anywhere herein.

In some embodiments, in the compound of Formula (VI), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl. In some embodiments, $R^2$ is H. In some embodiments, $R^3$ is H. In other embodiments, $R^2$ is H and $R^3$ is H.

In some embodiments, in the compound of Formula (VI), p is 0. In some embodiments, q is 0. In other embodiments, p is 0 and q is 0.

In some embodiments, in the compound of Formula (VI), U is N.

In some embodiments, the compound of the invention is:

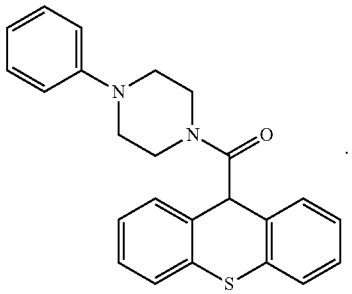

(3)

In another embodiment, $R^1$ is selected from the group consisting of phenyl, quinolinyl and isoquinolinyl, each of which may independently be unsubstituted or substituted with one or more halogen, $OR^a$ or $NR^aR^b$ wherein $R^a$ and $R^b$ are each independently selected from the group consisting of H or a $C_1$-$C_4$ alkyl.

In another embodiment, $R^1$ is C(=O)—$OR^a$ wherein $R^a$ is a $C_1$-$C_4$ alkyl. In other embodiments, $R^1$ is selected from the group consisting of:
a) phenyl;
b) fluorophenyl;
c) difluorophenyl;
d) pentafluorophenyl;
e) methoxyphenyl;

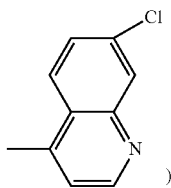

f; and
g) C(=O)—$OCH_2CH_3$.

Each possibility represents a separate embodiment of the present invention.

In some embodiments, in the compound of Formula (II) or in the compound of Formula (IV), X is S. In one embodiment, when X is S, Z is CH. In an alternative embodiment, the following compound is excluded: a compound of Formula (II) wherein X is S, Z is N, Y is C=O, n is 0, m is 0, $R^1$ is an unsubstituted or substituted phenyl and p and q are each 0. In another embodiment, the following compound is excluded: a compound of formula (II) wherein X is S, Z is N, Y is C=O, n is 0, m is 0, $R^1$ is pyridinyl and p and q are each 0.

In some embodiments wherein X is S, $R^1$ is aryl, optionally substituted with one or more alkyl, arylalkyl, halogen, $NO_2$, CN, $OR^4$, and $NR^{5a}R^{5b}$, or a combination thereof. In some embodiments wherein X is S, $R^1$ is aryl substituted with one or more alkyl, arylalkyl, halogen, $NO_2$, CN, $OR^4$, and $NR^{5a}R^{5b}$, or a combination thereof. In some embodiments wherein X is S. $R^1$ is aryl substituted with one or more alkyl, arylalkyl, halogen, $NO_2$, and $NR^{5a}R^{5b}$, or a combination thereof. In some embodiments wherein X is S, $R^1$ is phenyl substituted with one or more alkyl, arylalkyl, halogen, $NO_2$, and $NR^{5a}R^{5b}$, or a combination thereof. In some embodiments wherein X is S, $R^1$ is aryl, optionally substituted with one or more halogen and $C_1$-$C_4$ alkyl, or a combination thereof. In some embodiments wherein X is S, $R^1$ is phenyl, optionally substituted with one or more halogen and $C_1$-$C_4$ alkyl, or a combination thereof.

In some embodiments wherein X is S, $R^1$ is heteroaryl, optionally substituted with one or more alkyl, arylalkyl, halogen, $NO_2$, CN, $OR^4$, and $NR^{5a}R^{5b}$, or a combination thereof. In some embodiments wherein X is S, $R^1$ is not pyridinyl. In some embodiments wherein X is S. $R^1$ is heteroaryl substituted with one or more alkyl, arylalkyl, halogen, $NO_2$, CN, $OR^4$, and $NR^{5a}R^{5b}$, or a combination thereof. In some embodiments wherein X is S, $R^1$ is heteroaryl substituted with one or more alkyl, arylalkyl, halogen, $NO_2$, and $NR^{5a}R^{5b}$, or a combination thereof. In some embodiments wherein X is S, $R^1$ is quinolinyl, or isoquinolinyl. In some embodiments wherein X is S, $R^1$ is quinolinyl or isoquinolinyl, optionally substituted with one or more alkyl, arylalkyl, halogen, $NO_2$, CN, $OR^4$, and $NR^{5a}R^{5b}$, or a combination thereof. In some embodiments wherein X is S, $R^1$ is quinolinyl or isoquinolinyl, optionally substituted with one or more halogen and $C_1$-$C_4$ alkyl, or a combination thereof. In certain embodiments wherein X is S, $R^1$ is C(=O)—$OR^a$, wherein $R^a$ is $C_1$-$C_4$ alkyl.

In one embodiment, the compound represented by the structure of Formula (II) as described herein is as described but having the proviso that:
(1) when Z is CH, X is NH, S, or a bond;
(2) when X is S. Z is CH; and
(3) the following compound: a compound of Formula (II) wherein X is NH, Z is CH, Y is C=O, n is 0, m is 0, $R^1$ is a phenyl substituted by one or more alkoxy, and p and q are each 0, is excluded.

In another embodiment, the compound represented by the structure of Formula (II) as described herein is as described but having the proviso that:
(1) when Z is CH, X is NH, S, or a bond and (2) the following compounds are excluded:
(i) a compound of Formula (II) wherein X is NH, Z is CH, Y is C=O, n is 0, m is 0, R1 is a phenyl substituted by one or more alkoxy, and p and q are each 0; and
(ii) a compound of Formula (II) wherein X is S, Z is N, Y is C=O, n is 0, m is 0, R1 is an unsubstituted or substituted phenyl and p and q are each 0.

In another embodiment, the compound represented by the structure of Formula (II) as described herein is as described but having the proviso that:
(1) when Z is CH, X is NH, S, or a bond;
(2) the following compounds are excluded:
(i) a compound of formula (II) wherein X is NH, Z is CH, Y is C=O, n is 0, m is 0, $R^1$ is a phenyl substituted by one or more alkoxy, and p and q are each 0; and
(ii) a compound of formula (II) wherein X is S, Z is N, Y is C=O, n is 0, m is 0, $R^1$ is pyridinyl and p and q are each 0.

In one embodiment, the compound is represented by Formula (II), wherein n is 0. According to this aspect and in one embodiment, the compound is represented by the structure of Formula (II-a):

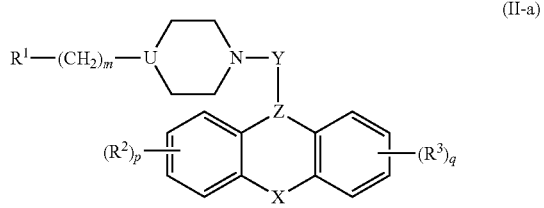
(II-a)

In another embodiment, the compound is represented by Formula (II) wherein X is O, Z is N, Y is C=O, n is 0, m is 0, $R^1$ is phenyl or methoxyphenyl and p and q are each 0.

In yet another embodiment, the compound is represented by Formula (II) wherein X is S, Z is CH, Y is C=O, n is 0, m is 0, $R^1$ is phenyl and p and q are each 0.

In one embodiment, the compound is represented by Formula (II) wherein X is O, Z is N, Y is C=O, n is 0, m is 0, $R^1$ is methoxyphenyl and p and q are each 0. In another embodiment, the compound is represented by Formula (II), wherein X is O, Z is N, Y is C=O, n is 0, m is 0, $R^1$ is difluorophenyl or pentafluorophenyl and p and q are each 0.

In another embodiment the compound is represented by Formula (II), wherein p and q are each 0 (i.e., $R^2$ and $R^3$ do not exist).

As demonstrated herein, said compound has unexpectedly been found to be a highly potent and selective cytotoxic agent, exhibiting selective cytotoxicity towards cancer as well as pre-cancerous cells and benign hyperproliferative disorders, while having little effect on normal cells.

As used herein, in some embodiments, an "alkyl" group refers to any saturated aliphatic hydrocarbon, including straight-chain and branched-chain alkyl groups. In one embodiment, the alkyl group has 1-4 carbons designated here as $C_1$-$C_4$-alkyl. In some embodiments, the alkyl group has 1-7 carbons designated here as $C_1$-$C_7$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group denotes a heteroaromatic system containing at least one heteroatom ring atom selected from nitrogen, sulfur and oxygen. The heteroaryl contains 5 or more ring atoms. In some embodiments, the heteroaryl group contains 5-10 ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, quinolyl (e.g. 1-quinolinyl, 2-quinolinyl, 3-quinolinyl, 4-quinolinyl, 5-quinolinyl, 6-quinolinyl, 7-quinolinyl and 8-quinolinyl), isoquinolinyl (e.g., 1-isoquinolinyl, 2-isoquinolinyl, 3-isoquinolinyl, 4-isoquinolinyl, 5-isoquinolinyl, 6-isoquinolinyl, 7-isoquinolinyl and 8-isoquinolinyl); naphthyridinyl (e.g., 1-naphthyridinyl, 2-naphthyridinyl), quinoxalinyl, quinazolinyl, cinnolinyl, pteridinyl, carbolinyl, thiazolyl, oxazolyl, isothiazolyl, isoxazolyl and the like. The heteroaryl group can optionally be substituted through available atoms with one or more groups defined hereinabove for alkyl. The heteroaryl group can be unsubstituted or substituted through available atoms with one or more groups defined hereinabove for alkyl.

The term "halogen" or "halo" as used herein alone or as part of another group refers to chlorine, bromine, fluorine, and iodine.

The term "hydroxy" refers to an OH group. The terms "alkoxy" refers to the group $OR^a$ wherein $R^a$ is a $C_1$-$C_4$ alkyl as defined above. Nonlimiting examples of an alkoxy group is methoxy, ethoxy, n-propoxy, isopropoxy, n-butoxy, t-butoxy and like groups.

All stereoisomers of the compounds of the instant invention are contemplated, either in admixture or in pure or substantially pure form. The compounds of the present invention can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R, S or d, D, l, L or d, l, D, L. The present invention intends to encompass all structural and geometrical isomers including cis, trans, E and Z isomers.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the invention.

The term "organic or inorganic cation" refers to counterions for the anion of a salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl) ammonium, phenylethylbenzylammonium, dibenzylethylene diammonium, and like cations. See, for example, "Pharmaceutical Salts," Berge et al., J. Pharm. Sci., 66:1-19 (1977), which is incorporated herein by reference.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline state of a substance, which can be characterized by particular physical properties such as X-ray diffraction, IR spectra, melting point, and the like.

The present invention provides stable topical pharmaceutical compositions comprising a compound of Formula (II), and methods of using these compositions, especially for treating or preventing cancer or a pre-cancerous condition, or a benign hyperproliferative disorder, e.g., actinic keratosis.

Therapeutic Use

The compounds of the present invention are significantly more potent than the compounds disclosed in the art, and exert selective cytotoxicity on cancerous cells, e.g. prostate cancer cells, pancreatic carcinoma cells, colon carcinoma cells, cervix adenocarcinoma cells, lung carconima cells, as well as pre-cancerous cells, while having a very small effect on normal cells. As such, the compounds of the present invention are useful in inhibiting cancer cell proliferation and treating a variety of cancers.

As described herein, the compounds of the present invention are potent cytotoxic agents that are capable of inhibiting cell proliferation in a wide variety of hyper-proliferating cells, such as cancer cells as well as pre-cancer cells and cells associated with benign hyperproliferative disorders. The present invention thus provides powerful methods to the chemoprevention and treatment of cancer, pre-cancer and benign hyperproliferative disorders that have not been previously described.

In one aspect, the present invention features a method for treating cancer, a pre-cancerous condition or a benign hyperproliferative disorder in a subject in need thereof, comprising the step of administering to the subject a therapeutically effective amount of a compound represented by the structure of Formula (II), or a pharmaceutically acceptable salt thereof:

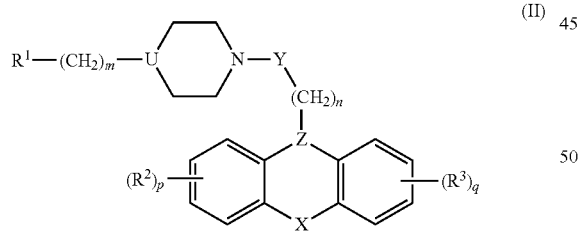

(II)

wherein
U and Z are each independently N or CH;
X is O, NH, S, or a bond;
Y is $CH_2$, C=O, or C=S;
$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$, or a combination thereof;
$R^2$ and $R^3$ are each independently at each occurrence selected from the group consisting of: halogen, $NO_2$, CN, $C_1$-$C_4$ alkyl, $OR^4$, and $NR^{5a}R^{5b}$;
$R^4$, $R^a$, $R^{5a}$, and $R^{5b}$ are each independently hydrogen or $C_1$-$C_4$ alkyl;

n is 0 or 1;
m is 0, 1, or 2;
p and q are each independently selected from 0, 1, 2, 3, and 4; and
or a pharmaceutically acceptable salt thereof.

In one embodiment, the composition includes salts, hydrates, solvates, polymorphs, optical isomers, geometrical isomers, enantiomers, diastereomers, and mixtures thereof.

In one embodiment, when Z is CH, X is not O. In another embodiment, when Z is CH, X is NH, S, or a bond.

In another embodiment, Z is N, and U is N or CH.

In another embodiment, the following compounds are excluded:
(i) a compound of Formula (II) wherein X is NH, Z is CH, Y is C=O, n is 0, m is 0, $R^1$ is a phenyl substituted by one or more alkoxy, and p and q are each 0; and
(ii) a compound of Formula (II) wherein X is S, Z is N, Y is C=O, n is 0, m is 0, $R^1$ is an unsubstituted or substituted phenyl and p and q are each 0.

In some embodiments, in the compound of Formula (II), m and n are each 0.

In some embodiments, in the compound of Formula (II), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, in the compound of Formula (II), p is 0. In some embodiments, q is 0. In other embodiments, p is 0 and q is 0.

In some embodiments, in the compound of Formula (II), U is N.

In some embodiments, the compound of the invention is represented by a compound of Formula (III)

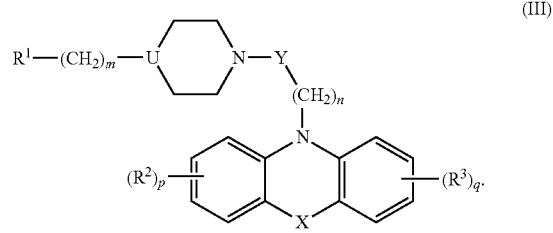

(III)

wherein X, U, $R^1$, $R^2$, $R^3$, m, n, p, and q are defined as anywhere herein.

In some embodiments, in the compound of Formula (III), X is O, NH, or a bond. In some embodiments, X is O. In other embodiments, X is a bond. In certain embodiments, X is NH.

In some embodiments, in the compound of Formula (III), m and n are each 0.

In some embodiments, in the compound of Formula (III), $R^1$ is aryl or heteroaryl. In some embodiments, $R^1$ is phenyl, quinolinyl, or isoquinolinyl. In other embodiments, $R^1$ is phenyl, optionally substituted with one or more halogen, CN, $C_1$-$C_4$ alkyl, $OR^4$, or a combination thereof. In certain embodiments, $R^1$ is C(=O)—$OR^a$, wherein $R^a$ is $C_1$-$C_4$ alkyl.

In some embodiments, $R^2$ is H. In some embodiments, $R^3$ is H. In other embodiments,
$R^2$ is H and $R^3$ is H.

In some embodiments, in the compound of Formula (III), p is 0. In some embodiments, q is 0. In other embodiments, p is 0 and q is 0.

In some embodiments, in the compound of Formula (III), U is N.

In some embodiments, the compound of invention is represented by a compound of Formula (IV)

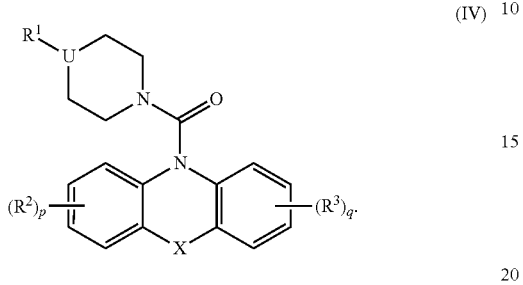

(IV)

wherein X, U, R$^1$, R$^2$, R$^3$, m, n, p, and q are defined as anywhere herein.

In some embodiments, in the compound of Formula (IV), X is O. In other embodiments, X is S. In certain embodiments, X is NH.

In some embodiments, in the compound of Formula (IV), R$^1$ is aryl or heteroaryl. In some embodiments, R$^1$ is phenyl, quinolinyl, or isoquinolinyl. In other embodiments, R$^1$ is phenyl, optionally substituted with one or more halogen, CN, C$_1$-C$_4$ alkyl, OR$^4$, or a combination thereof. In certain embodiments, R$^1$ is C(=O)—OR$^a$, wherein R$^a$ is C$_1$-C$_4$ alkyl.

In some embodiments, R$^2$ is H. In some embodiments, R$^3$ is H. In other embodiments, R$^2$ is H and R$^3$ is H.

In some embodiments, in the compound of Formula (IV), p is 0. In some embodiments, q is 0. In other embodiments, p is 0 and q is 0.

In some embodiments, in the compound of Formula (IV), U is N.

In some embodiments, the compound of the invention is:

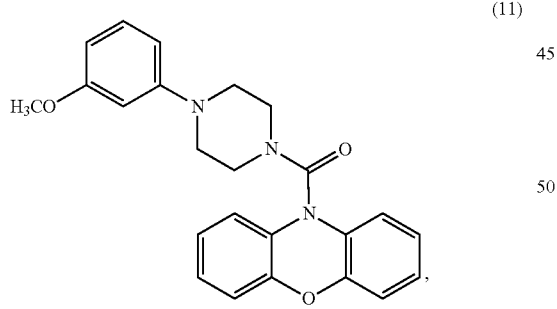

(11)

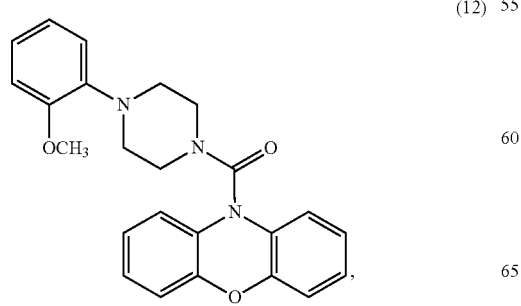

(12)

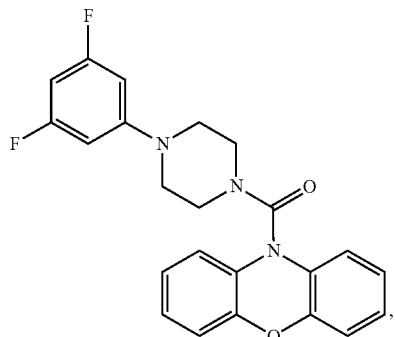

(13)

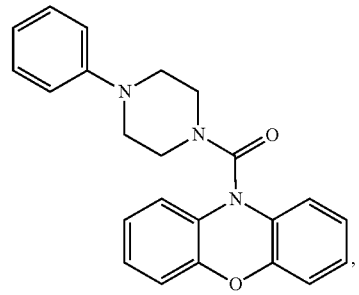

(1)

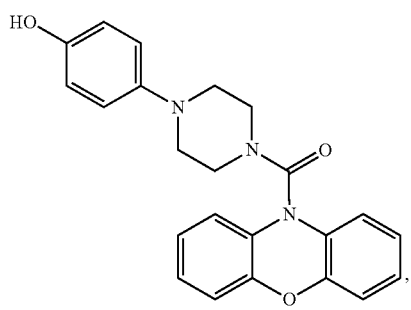

(14)

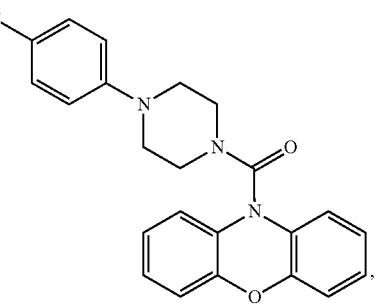

(15)

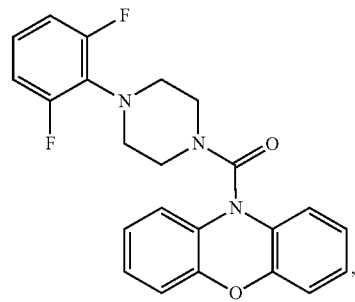

(5)

-continued

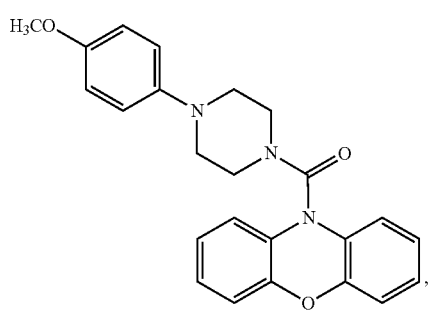
(4)

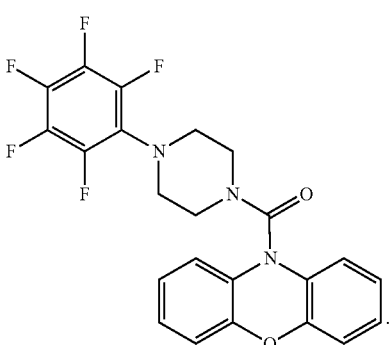
(16), or

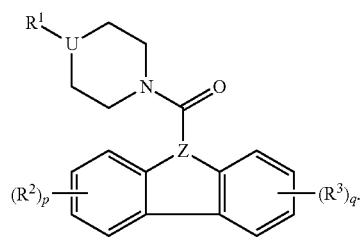
(2)

In some embodiments, the compound of the invention is represented by a compound of Formula (V)

(V)

wherein X, U, R$^1$, R$^2$, R$^3$, m, n, p, and q are defined as anywhere herein.

In some embodiments, in the compound of Formula (V), Z is N. In other embodiments, Z is CH.

In some embodiments, in the compound of Formula (V), R$^1$ is aryl or heteroaryl. In some embodiments, R$^1$ is phenyl, quinolinyl, or isoquinolinyl. In other embodiments, R$^1$ is phenyl, optionally substituted with one or more halogen, CN, C$_1$-C$_4$ alkyl, OR$^4$, or a combination thereof. In certain embodiments, R$^1$ is C(=O)—OR$^a$, wherein R$^a$ is C$_1$-C$_4$ alkyl. In some embodiments, R$^2$ is H. In some embodiments, R$^3$ is H. In other embodiments, R$^2$ is H and R$^3$ is H.

In some embodiments, in the compound of Formula (V), p is 0. In some embodiments, q is 0. In other embodiments, p is 0 and q is 0.

In some embodiments, in the compound of Formula (V), U is N.

In some embodiments, the compound of the invention is:

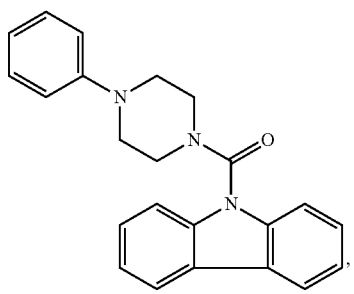
(20)

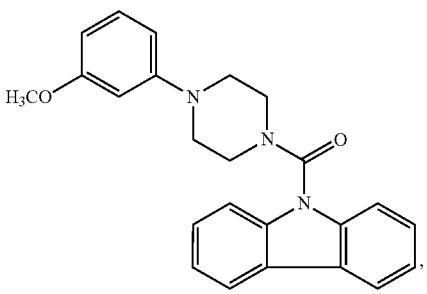
(21)

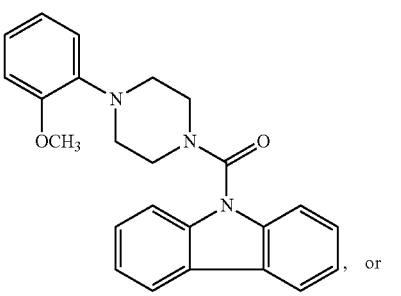
(22), or

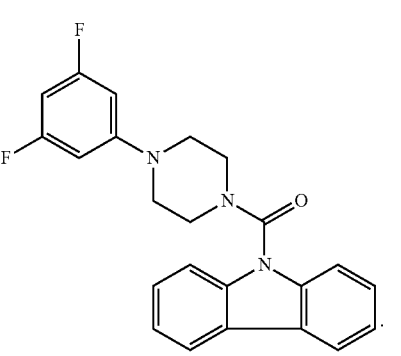
(23)

In some embodiments, the compound of the invention is represented by a compound of Formula (VI)

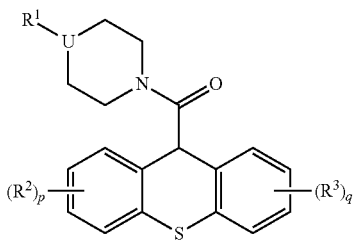

(VI)

wherein U, R¹, R², R³, p, and q are defined as anywhere herein.

In some embodiments, in the compound of Formula (VI), R¹ is aryl or heteroaryl. In some embodiments, R¹ is phenyl, quinolinyl, or isoquinolinyl. In other embodiments, R¹ is phenyl, optionally substituted with one or more halogen, CN, $C_1$-$C_4$ alkyl, $OR^4$, or a combination thereof. In certain embodiments, R¹ is C(=O)—$OR^a$, wherein $R^a$ is $C_1$-$C_4$ alkyl. In some embodiments, R² is H. In some embodiments, R³ is H. In other embodiments, R² is H and R³ is H.

In some embodiments, in the compound of Formula (VI), p is 0. In some embodiments, q is 0. In other embodiments, p is 0 and q is 0.

In some embodiments, in the compound of Formula (VI), U is N.

In some embodiments, the compound of the invention is:

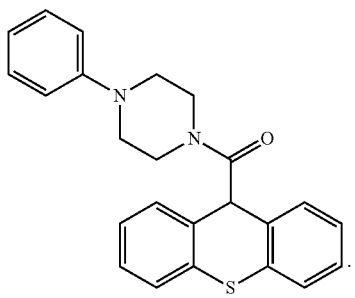

(3)

In some embodiments, in the method of the invention, the subject is a mammal. In some embodiments, the mammal is a human.

In some embodiments, in the method of the invention, the cancer comprises a solid tumor. In one embodiment, the solid tumor comprises prostate cancer. In another embodiment, the solid tumor comprises pancreatic cancer. In another embodiment, the solid tumor comprises colon cancer, cervical cancer, lung cancer, breast cancer, liver cancer, skin cancer, melanoma, or metastases thereof. Each possibility represents a separate embodiment of the present invention.

In some embodiments, in the method of the invention, the cancer comprises squamous cell carcinoma (SCC), basal cell carcinoma (BCC), cutaneous T-cell lymphoma (CTCL), or metastases thereof. Each possibility represents a separate embodiment of the present invention.

In one embodiment, the compounds of the present invention are active against a wide range of cancers, including but not limited to: colon cancer, cervical cancer, lung cancer, pancreatic cancer, breast cancer, liver cancer, skin cancer, melanoma, lymphoproliferative disorders, ovarian cancer, prostate cancer, endometrial cancer, bone cancer, stomach cancer, cancer of the thyroid, head and neck cancer, cancer of the central nervous system, cancer of the peripheral nervous system, kidney cancer, hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, adenocarcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic and hematologic malignancies, or metastases thereof. In one embodiment, the hematologic malignancy comprises leukemia, lymphoma, multiple myeloma, or metastases thereof.

In some embodiments, leukemia includes acute myelogenous leukemia, acute myelocytic leukemia, acute lymphocytic leukemia, acute lymphoblastic leukemia, chronic myelogenous leukemia, chronic lymphocytic leukemia, and mast cell leukemia, or metastases thereof. In some embodiments, lymphoma includes myeloid lymphoma, Hodgkin's lymphoma, and non-Hodgkin's lymphoma, or metastases thereof. Each possibility represents a separate embodiment of the present invention.

In some embodiments, lung cancer comprises lung carcinoma. In one embodiment, the lung carcinoma comprises small cell carcinoma. In another embodiment, the lung carcinoma comprises non-small carcinoma. In another embodiment, the lung carcinoma comprises large cell lung carcinoma. In some embodiments, adenocarcinoma is well differentiated, moderately differentiated, poorly differentiated or undifferentiated.

In another embodiment, the methods and uses of the invention as described herein comprise treating a cancer described hereinabove.

In some embodiments, in the method of the invention, the compound is administered in combination with at least one other agent effective at treating cancer, a pre-cancer condition or a hyperproliferative disorder. In some embodiments, the compound is formulated for parenteral administration, oral administration, rectal administration, intranasal administration, topical administration, administration by inhalation, or administration via a suppository. In some embodiments, the parenteral administration is intravenous, subcutaneous, intraperitoneal, intraarterial, transdermal, or intramuscular administration. In certain embodiments, the compound is formulated for intravenous administration.

In another aspect, the present invention provides a method for inhibiting cancer or pre-cancer cell proliferation in vitro, comprising contacting the cancer cells with a therapeutically effective amount of a compound of the present invention, as described herein. In some embodiments, the compound is one or more of the compounds represented by Formula (II), (III), (IV), or (V). In some embodiments, the compound is one or more of the compounds represented by Compound 20, 21, 22, or 23. In some embodiments, the compound is one or more of Compound 11, 12, 13, 14, 15, or 16. In some embodiments, the compound is one or more of the compounds represented by Compound 1, 2, 3, 4, or 5. In some embodiments, the compound is administered in a pharmaceutical composition.

The present invention provides a method for the treatment of cancer, a pre-cancerous condition or a benign hyperproliferative disorder in a subject in need thereof, by administering to the subject a therapeutically effective amount of the compound of the invention, as described herein. In some embodiments, the compound is one or more of the compounds represented by Formula (II), (III), (IV), or (V). In some embodiments, the compound is one or more of the compounds represented by Compound 20, 21, 22, or 23. In some embodiments, the compound is one or more of Compound 11, 12, 13, 14, 15, or 16. In some embodiments, the compound is one or more of the compounds represented by Compound 1, 2, 3, 4, or 5. In some embodiments, the compound is administered in a pharmaceutical composition.

The present invention provides a method for the treatment of cancer, a pre-cancerous condition or a benign hyperproliferative disorder in a subject in need thereof, by administering to the subject a therapeutically effective amount of the compound of the invention, as described herein. In some embodiments, the compound is one or more of the compounds represented by Formula (II), (III), (IV), or (V). In some embodiments, the compound is one or more of the compounds represented by Compound 20, 21, 22, or 23. In some embodiments, the compound is one or more of Compound 11, 12, 13, 14, 15, or 16. In some embodiments, the compound is one or more of the compounds represented by Compound 1, 2, 3, 4, or 5. In some embodiments, the compound is administered in a pharmaceutical composition.

In another aspect, the present invention relates to the use of a compound represented by general Formula (II), (III), (IV), or (V), or one or more of the compounds represented by Compound 20, 21, 22, or 23, or one or more of Compound 11, 12, 13, 14, 15, or 16, or one or more of Compound 1, 2, 3, 4, or 5, or a pharmaceutical composition comprising such compound, in the preparation of a medicament useful for the treatment of cancer, a pre-cancerous condition or a benign hyperproliferative disorder.

The present invention further relates to a compound represented by general Formula (II), (III), (IV), and (V), or any of the compounds exemplified by these formulae, or Compound 20, 21, 22, or 23, Compound 11, 12, 13, 14, 15, or 16, Compound 1, 2, 3, 4, or 5, or a pharmaceutical composition comprising such compound, for the use in the treatment of cancer, a pre-cancer condition or benign hyperproliferative disorder.

In one embodiment, the subject is a mammal. In some embodiments, the subject is a human. However, the present invention also contemplates using the compounds of the present invention for non-human mammals, e.g., in veterinary medicine. In one embodiment, the subject is murine, bovine, ovine, canine, feline, equine, porcine, etc. In one embodiment, the compositions and methods of the present invention are effective in male subjects. In another embodiment, the compositions and methods of the present invention are effective in female subjects.

It is to be understood that whenever the terms "treating or inhibiting a malignant cell proliferative disease or disorder", "treating or inhibiting a non-solid cancer", "treating or inhibiting a tumor" are used herein in the description and in the claims, they are intended to encompass tumor formation, primary tumors, tumor progression or tumor metastasis.

The term "inhibition of proliferation" in relation to cancer cells, in the context of the present invention refers to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastasis, reduction in the number of new metastasis formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. This term also encompasses prevention for prophylactic situations or for those individuals who are susceptible to contracting a tumor. The administration of the compounds of the present invention will reduce the likelihood of the individual contracting the disease. In preferred situations, the individual to whom the compound is administered does not contract the disease.

As used herein, the term "administering" refers to bringing in contact with a compound of the present invention. Administration can be accomplished to cells or tissue cultures, or to living organisms, for example humans.

A "therapeutic" treatment is a treatment administered to a subject who exhibits signs of pathology for the purpose of diminishing or eliminating those signs. A "therapeutically effective amount" of a compound of the invention is that amount of compound which is sufficient to provide a beneficial effect to the subject to which the compound is administered.

The term "cancer" in the context of the present invention includes all types of neoplasm whether in the form of solid or non-solid tumors, and includes both malignant and pre-malignant conditions as well as their metastasis.

Cancers may be classified in two ways: by the type of tissue in which the cancer originates (histological type) and by primary site, or the location in the body where the cancer first developed. The international standard for the classification and nomenclature of histologies is the International Classification of Diseases for Oncology, Third Edition.

From a histological standpoint there are hundreds of different cancers, which are grouped into five major categories: carcinoma, sarcoma, myeloma, leukemia, and lymphoma. In addition, there are also some cancers of mixed types.

Carcinoma refers to a malignant neoplasm of epithelial origin or cancer of the internal or external lining of the body. Carcinomas, malignancies of epithelial tissue, account for 80 to 90 percent of all cancer cases. Epithelial tissue is found throughout the body. It is present in the skin, as well as the covering and lining of organs and internal passageways, such as the gastrointestinal tract.

Carcinomas are divided into two major subtypes: adenocarcinoma, which develops in an organ or gland, and squamous cell carcinoma, which originates in the squamous epithelium. Most carcinomas affect organs or glands capable of secretion, such as the breasts, which produce milk, or the lungs, which secrete mucus, or colon or prostate or bladder.

Adenocarcinomas generally occur in mucus membranes and are first seen as a thickened plaque-like white mucosa. They often spread easily through the soft tissue where they occur. Squamous cell carcinomas occur in many areas of the body.

Sarcoma refers to cancer that originates in supportive and connective tissues such as bones, tendons, cartilage, muscle, and fat. Generally occurring in young adults, the most common sarcoma often develops as a painful mass on the bone. Sarcoma tumors usually resemble the tissue in which they grow.

Examples of sarcomas are: Osteosarcoma or osteogenic sarcoma (bone); Chondrosarcoma (cartilage); Leiomyosarcoma (smooth muscle); Rhabdomyosarcoma (skeletal muscle); Mesothelial sarcoma or mesothelioma (membranous lining of body cavities); Fibrosarcoma (fibrous tissue); Angiosarcoma or hemangioendothelioma (blood vessels); Liposarcoma (adipose tissue); Glioma or astrocytoma (neurogenic connective tissue found in the brain); Myxosarcoma (primitive embryonic connective tissue); Mesenchymous or mixed mesodermal tumor (mixed connective tissue types);

Myeloma is cancer that originates in the plasma cells of bone marrow. The plasma cells produce some of the proteins found in blood.

Leukemias ("non-solid tumors" or "blood cancers") are cancers of the bone marrow (the site of blood cell production). The disease is often associated with the overproduction of immature white blood cells. Leukemia also affects red blood cells and can cause poor blood clotting and fatigue due to anemia. Examples of leukemia include: Myelogenous or granulocytic leukemia (malignancy of the myeloid and granulocytic white blood cell series); Lymphatic, lymphocytic, or lymphoblastic leukemia (malignancy of the lymphoid and lymphocytic blood cell series); Polycythemia vera or erythremia (malignancy of various blood cell products, but with red cells predominating)

Lymphomas develop in the glands or nodes of the lymphatic system, a network of vessels, nodes, and organs (specifically the spleen, tonsils, and thymus) that purify bodily fluids and produce infection-fighting white blood cells, or lymphocytes. Unlike the leukemias, which are sometimes called "non-solid tumors," lymphomas are "solid cancers." Lymphomas may also occur in specific organs such as the stomach, breast or brain. These lymphomas are referred to as extranodal lymphomas. The lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma.

Mixed Type cancers contain several types of cells. The type components may be within one category or from different categories. Some examples are: adenosquamous carcinoma; mixed mesodermal tumor; carcinosarcoma and teratocarcinoma.

As used herein, the term "cancer" includes the above categories of carcinoma, sarcoma, myeloma, leukemia, lymphoma and mixed type tumors.

In some embodiments, the cancer is selected from the group consisting of squamous cell carcinoma, basal cell carcinoma, skin cancer, head and neck cancer, esophageal carcinoma, rectal carcinoma, cervical cancer, non-small cell lung carcinoma (NSCLC), cutaneous T-cell lymphoma (CTCL), breast cancer as well as metastases of all of the above. Each possibility represents a separate embodiment of the present invention.

It is contemplated that the compounds of the invention will be administered as stand-alone agents. However, in other embodiments, the compounds of the present invention will be administered in combination with additional anti-cancer agents known in the art. Thus, in other embodiments of the use of preparing a medicament, the medicament additionally comprises at least one active chemotherapeutic agent other than the compounds of the invention. In certain embodiments, the compounds of the invention may be administered alongside with at least one traditional chemotherapeutic drug that is effective at treating the particular cancer or pre-cancer or benign hyperproliferative disorder. The administration can be concurrent (either combined in one dosage form or in separate dosage forms) or sequential. If provided sequentially, the piperazine derivative can be administered before or after treatment with the additional chemotherapeutic agent(s). The combination of a compound of the invention and the traditional drug may allow administration of a lower dosage of the traditional drug, and thus the side effects experienced by the subject may be significantly lower, while a sufficient chemotherapeutic effect is nevertheless achieved.

The term "pre-cancer" or "pre-malignant" as used herein interchangeably refers to diseases, syndromes or other conditions associated with an increased risk of cancer. Pre-cancer conditions in the context of the present invention include, but are not limited to: breast calcifications, vaginal intra-epithelial neoplasia, actinic keratosis, Barrett's esophagus, atrophic gastritis, dyskeratosis congenital, sideropenic dysphagia, lichen planus, oral sibmucous fibrosis, solar elastosis, cervical desplasia, leukoplakia and erythroplakia.

The term "benign hyperproliferative disorder" as used herein refers to a condition in which there is an abnormal growth and differentiation of cells and an increase in the amount of organic tissue that results from cell proliferation. The benign hyperproliferative disorder may be attributed to lack of response or inappropriate response to regulating factors, or alternatively to dysfunctional regulating factors. Non-limiting example of benign hyperproliferative disorder are psoriasis and benign prostatic hyperplasia (BPH).

Pharmaceutical Compositions

Although the heterocyclic piperazine derivatives of the present invention can be administered alone, it is contemplated that these compounds will be administered in a pharmaceutical composition containing the piperazine derivative of the invention together with a pharmaceutically acceptable carrier or excipient. Thus, in another aspect, the present invention relates to a pharmaceutical composition comprising a compound as described anywhere herein, or a pharmaceutically acceptable salt thereof, and a pharmaceutically acceptable carrier.

The pharmaceutical compositions of the present invention can be formulated for administration by a variety of routes including oral, rectal, transdermal, parenteral (subcutaneous, intraperitoneal, intravenous, intraarterial, transdermal and intramuscular), topical, intranasal, or via a suppository, preferably suitable for intravenous administration. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material.

For intravenous administration, the compounds of the invention can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

The compositions can also be formulated for oral administration, e.g., in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, antibacterial agents, antioxidants (e.g., ascorbic acid or sodium bisulfite), chelating agents (e.g., ethylenediaminetetraacetic acid), and agents for the adjustment of tonicity such as sodium chloride.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Any method can be used to prepare the pharmaceutical compositions. Solid dosage forms can be prepared by wet granulation, dry granulation, direct compression and the like.

The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

In one embodiment, the active ingredient is dissolved in any acceptable lipid carrier (e.g., fatty acids, oils to form, for example, a micelle or a liposome).

Compositions for inhalation include solutions and suspensions in pharmaceutically acceptable aqueous or organic solvents, or mixtures thereof, and powders. The liquid or solid compositions may contain suitable pharmaceutically acceptable excipients as described above. In some embodiments, the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, for example, orally or nasally, from devices that deliver the formulation in an appropriate manner.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols.

Alternative formulations include nasal sprays, liposomal formulations, slow-release formulations, controlled-release formulations and the like, as are known in the art.

The compositions are in some embodiments formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. According to some embodiments, administration can be by direct injection e.g., via a syringe, at the site of a tumor or neoplastic or pre-neoplastic tissue.

The compounds may also be administered by any convenient route, for example by infusion or bolus injection, by absorption through epithelial linings (e.g., oral mucosa, rectal and intestinal mucosa, etc.), and may be administered together with other therapeutically active agents. In some embodiments, administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88:507; Saudek et al., 1989, N. Engl. J. Med. 321:574). In a preferred form, a compound of the invention is administered in combination with a biodegradable, biocompatible polymeric implant, which releases the compound over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Furthermore, at times, the pharmaceutical compositions may be formulated for parenteral administration (subcutaneous, intravenous, intraarterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

Alternatively, the piperazine derivatives of the present invention can be used in hemodialysis such as leukophoresis and other related methods, e.g., blood is drawn from the patient by a variety of methods such dialysis through a column/hollow fiber membrane, cartridge etc., is treated with the piperazine derivatives Ex-vivo, and returned to the patient following treatment. Such treatment methods are well known and described in the art. Sec, e.g., Kolho et al. (J. Med. Virol. 1993, 40 (4): 318-21); Ting et al. (Transplantation, 1978, 25 (1): 31-3); the contents of which are hereby incorporated by reference in their entirety.

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. A preferred dosage will be within the range of 0.01-1000 mg/kg of body weight, more preferably, 0.1 mg/kg to 100 mg/kg and even more preferably 1 mg/kg to 10 mg/kg. Effective doses may be extrapolated from dose-response curves derived from in vitro or animal model test bioassays or systems.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Experimental Set Up

The piperazine-derivatives were prepared as a stock of 50 mM in 100% DMSO (dimethyl sulfoxide). Piperazine-derivatives were added at concentration ranging from 0.03-10 uM for 72 hours. Each experimental point was performed in triplicates. Vehicle (DMSO)-treated cells were used as control. Dilutions were performed in culture medium and DMSO so that the final concentration of DMSO in each well was 0.5%. This 0.5% DMSO in medium (vehicle) by itself did not affect the viability of any of the cell lines.

Optical density representing viable cells was determined using the XTT Cell Proliferation Kit assay (sodium 2,3,-bis (2-methoxy-4-nitro-5-sulfophenyl)-5-[(phenylamino)-carbonyl]-2H-tetrazolium inner salt, Biological industries, Beit-Haemek, Israel).

Percentage of Optical density is directly proportional to the number of living cells in culture. Cytotoxicity (%) was calculated in the following way: [(OD of drug-treated cells-OD of background)/(OD of control cells-OD of background)]×100.

Example 1

Cytotoxicity of Piperazine Derivatives in Several Carcinoma Cell Lines

New piperazine derivatives were tested for cytotoxicity in 4 cancer cell lines:

A) HCT116—Human colon carcinoma cell-line
B) Hela—Human cervix adenocarcinoma cell-line
C) H358—Human lung carcinoma cell-line
D) Panc-1—Human pancreatic carcinoma cell-line Results:

IC 50 values for the different compounds in different cell lines are listed in Table 1 below.

TABLE 1

IC50 values for select compounds of the invention in various cancer cell lines.

| Compound | IC50 (XTT, 72 hr), µM | | | |
|---|---|---|---|---|
| | Colon HCT116 | Cervix Hela | Lung H358 | Pancreatic Panc-1 |
| 1 | 0.01 | 0.015 | 0.05 | 0.01 |
| 2 | | 1.9 | | >30 |
| 3 | 0.64 | 0.5 | 1.35 | 0.31 |
| 4 | 0.86 | 1.6 | 2.77 | 1.47 |
| 5 | 1.08 | 0.4 | 0.84 | 0.9 |

Example 2

Cytotoxicity of Additional Piperazine Derivatives in Lung Carcinoma Cells

New piperazine derivatives (compounds of Formula (IV)) were tested for cytotoxicity in the H358 human lung carcinoma cell line. Table 2 below provides IC50 values for the tested compounds.

TABLE 2

IC50 values for select compounds of the invention in a lung cancer cell line.
Conditions: H358 lung cancer line, 11.5 mM glucose, 5000 cell/well, 0.5% FCS, 72 hours.

| Compound | Structure | IC50 (µM) |
|---|---|---|
| 11 | 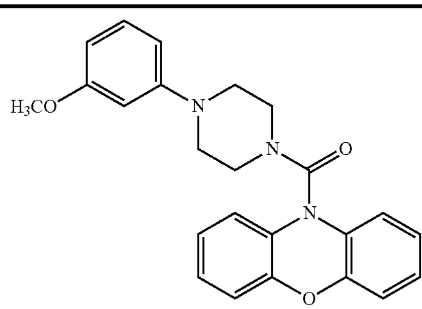 | 0.0047 |
| 12 | 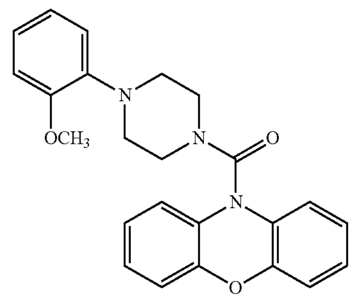 [SMILES: COc1ccccc1N1CCN(C(=O)N2c3ccccc3Oc3ccccc32)CC1] | 0.0066 |
| 13 | 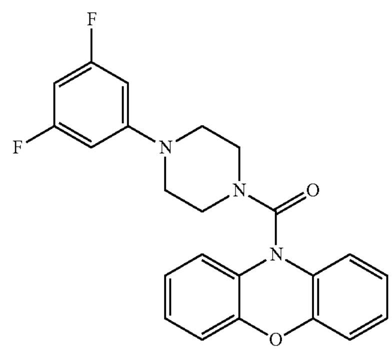 [SMILES: O=C(N1CCN(c2cc(F)cc(F)c2)CC1)N1c2ccccc2Oc2ccccc21] | 0.0067 |
| 1 | 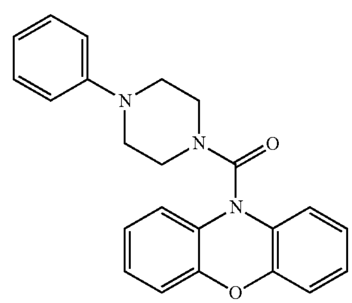 [SMILES: O=C(N1CCN(c2ccccc2)CC1)N1c2ccccc2Oc2ccccc21] | 0.025 |
| 14 | 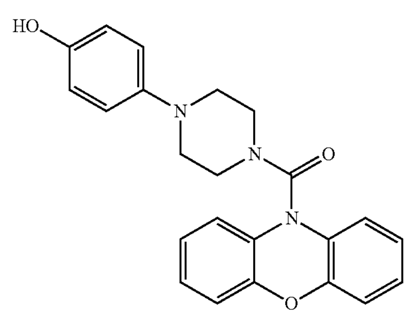 | 0.051 |

TABLE 2-continued

IC50 values for select compounds of the invention in a lung cancer cell line. Conditions: H358 lung cancer line, 11.5 mM glucose, 5000 cell/well, 0.5% FCS, 72 hours.

| Compound | Structure | IC50 (μM) |
|---|---|---|
| 15 | (15) | 0.24 |
| 5 | (5) | 0.265 |
| 4 | (4) | 1.00 |
| 16 | (16) | 1.37 |
| 2 | (2) | >10 |
| 3 | (3) | 0.43 |

New piperazine derivatives (compounds of Formula (V)) were tested for cytotoxicity in the H358 human lung carcinoma cell line. Table 3 below provide IC50 values for the tested compounds.

TABLE 3

IC50 values for select compounds of the invention in a lung cancer cell line. Conditions: H358 lung cancer line, 11.5 mM glucose, 5000 cell/well, 0.5% FCS, 72 hours

| Compound | Structure | IC$_{50}$ (μM) |
|---|---|---|
| 20 | (20) | 0.027 |

TABLE 3-continued

IC50 values for select compounds
of the invention in a lung cancer cell line.
Conditions: H358 lung cancer line,
11.5 mM glucose, 5000 cell/well, 0.5% FCS, 72 hours

| Compound | Structure | IC$_{50}$ (μM) |
|---|---|---|
| 21 | 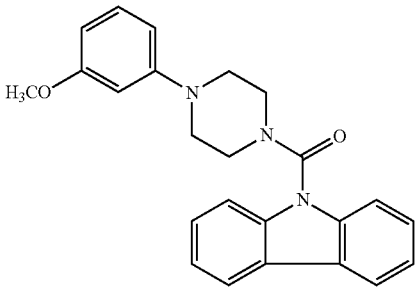 (21) | 0.063 |
| 22 | 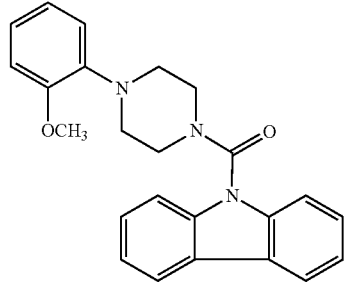 [SMILES: COc1ccccc1N1CCN(C(=O)n2c3ccccc3c3ccccc32)CC1] (22) | 0.003 |
| 23 | 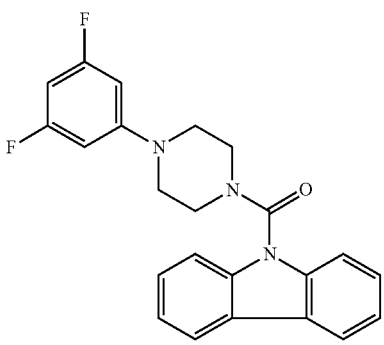 [SMILES: O=C(N1CCN(c2cc(F)cc(F)c2)CC1)n1c2ccccc2c2ccccc21] (23) | 0.009 |

New piperazine derivatives (compounds of Formula (IV) and Formula (V)) were tested for cytotoxicity in the H358 human lung carcinoma cell line. Table 4 below provide IC50 values for the tested compounds.

TABLE 4

IC50 values for select compounds
of the invention in a prostate cancer cell line.
Conditions: PC3 prostate cancer line,
25 mM glucose, 1500 cell/well, 10% FCS, 72 hours.

| Compound | Structure | IC$_{50}$ (μM) |
|---|---|---|
| 21 | 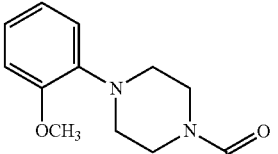 | 0.024 |
| 22 | 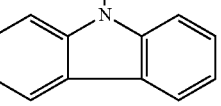 | 0.026 |
| 1 | 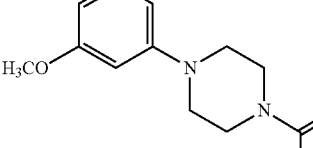 | 0.026 |
| 23 | 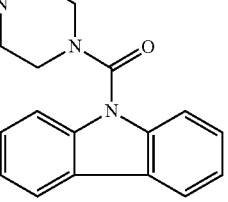 | 0.08 |

CONCLUSIONS

The piperazine derivatives shown herein are highly potent. The data suggest a possible therapeutic effect for new piperazine derivatives in a variety of cell lines, namely prostate cancer, pancreatic cancer, colon cancer, cervical cancer, and lung cancer.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A method for treating a cancer or for inhibiting cancer cell proliferation in a subject, wherein said cancer does not comprises-a lymphoma or a metastasis thereof, the method comprising administering to said subject a therapeutically effective amount of a compound represented by the structure of Formula (II), or a pharmaceutically acceptable salt thereof:

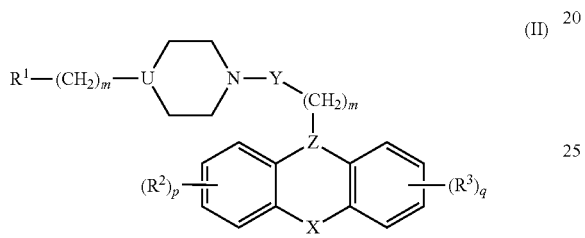

(II)

wherein:
U is N or CH;
when X is O, NH, or a bond, Z is N and
when X is S, Z is CH;
Y is $CH_2$, C=O, or C=S;
$R^1$ is aryl, heteroaryl, or C(=O)—$OR^a$, wherein aryl and heteroaryl are each optionally substituted with one or more alkyl, arylalkyl, halogen, $NO_2$, CN, $OR^4$, $NR^{5a}R^{5b}$, or a combination thereof;
$R^2$ and $R^3$ are each independently at each occurrence selected from the group consisting of: halogen, $NO_2$, CN, $C_1$-$C_4$ alkyl, $OR^4$, and $NR^{5a}R^{5b}$;
$R^4$, $R^a$, $R^{5a}$, and $R^{5b}$ are each independently hydrogen or $C_1$-$C_4$ alkyl;
n is 0 or 1;
m is 0, 1, or 2; and
p and q are each independently selected from 0, 1, 2, 3, and 4;
or a pharmaceutically acceptable salt thereof.

2. The method of claim 1, wherein m is 0.
3. The method of claim 1, wherein $R^1$ is aryl or heteroaryl.
4. The method of claim 1, wherein $R^1$ is phenyl, quinolinyl, or isoquinolinyl.
5. The method of claim 1, wherein $R^1$ is phenyl, optionally substituted with one or more halogen, CN, $C_1$-$C_4$ alkyl, $OR^4$, or a combination thereof.
6. The method of claim 1, wherein $R^1$ is C(=O)—$OR^a$, wherein $R^a$ is $C_1$-$C_4$ alkyl.
7. The method of claim 1, wherein p is 0.
8. The method of claim 1, wherein q is 0.
9. The method of claim 1, wherein U is N.
10. The method of claim 1, wherein X is O, NH, or a bond.
11. The method of claim 1, wherein said compound is a compound of Formula (V):

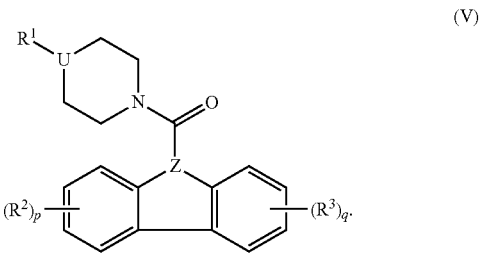

(V)

12. The method of claim 11, wherein Z is N.
13. The method of claim 12, wherein said compound is:

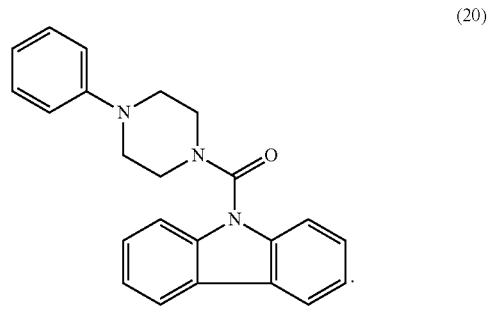 [SMILES: O=C(N1CCN(c2ccccc2)CC1)n1c2ccccc2c2ccccc21]

(20)

14. The method of claim 12, wherein said compound is:

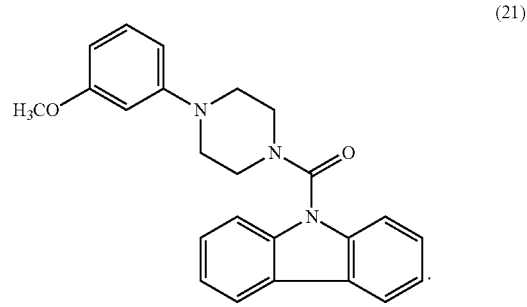 [SMILES: COc1cccc(N2CCN(C(=O)n3c4ccccc4c4ccccc43)CC2)c1]

(21)

15. The method of claim 12, wherein said compound is:

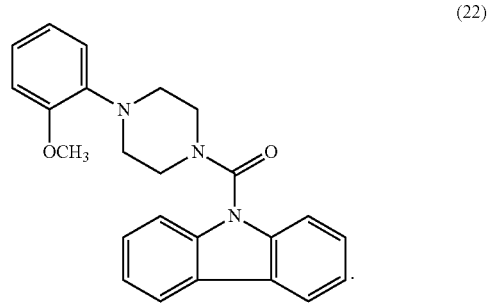 [SMILES: COc1ccccc1N1CCN(C(=O)n2c3ccccc3c3ccccc32)CC1]

(22)

16. The method of claim 12, wherein said compound is:
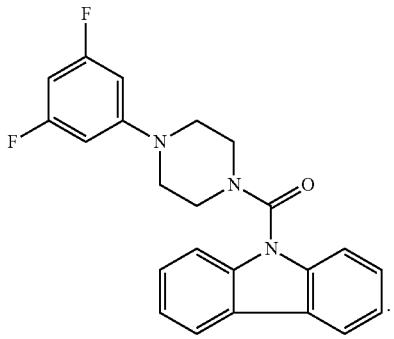
(23)
17. The method of claim 1, wherein said compound is a compound of Formula (III):
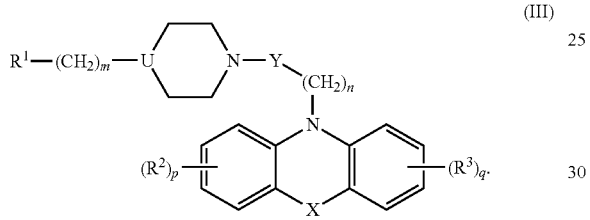
(III)
18. The method of claim 17, wherein said compound is a compound of Formula (IV):
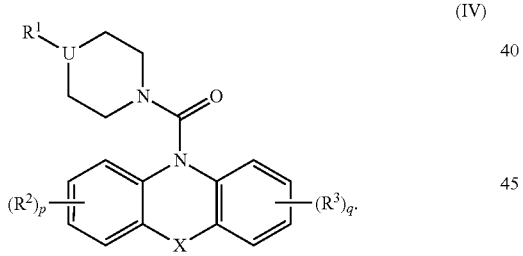
(IV)
19. The method of claim 18, wherein X is O.
20. The method of claim 19, wherein said compound is:
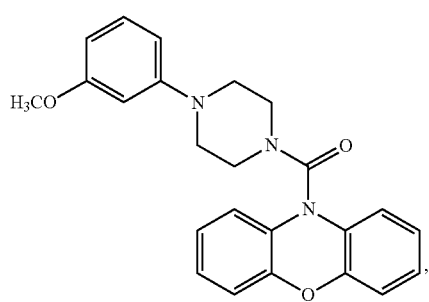
(11)
-continued
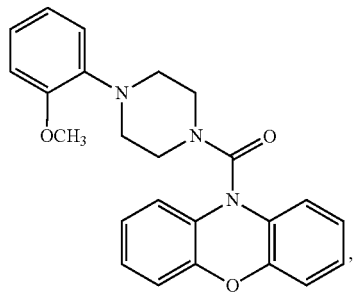
(12)
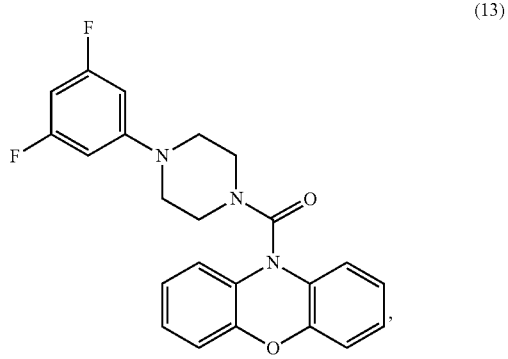
(13)
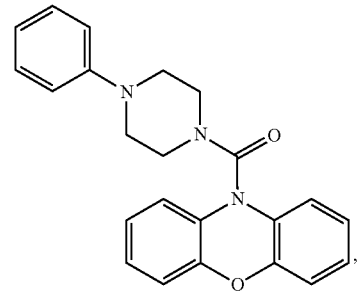
(1)
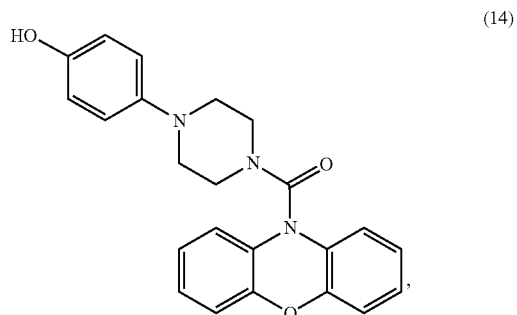
(14)
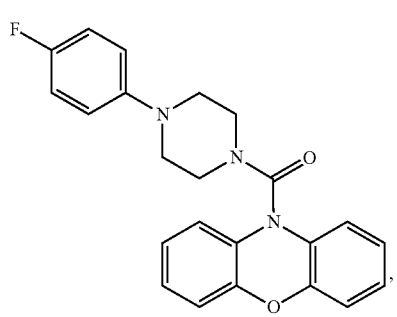
(15)

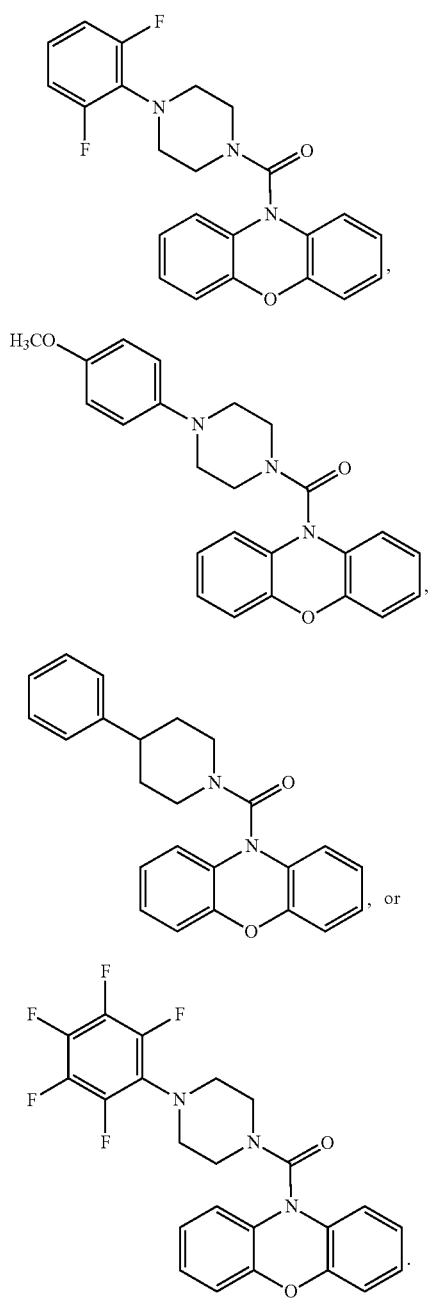

21. The method according to claim 1, wherein said compound is a compound of Formula (VI):

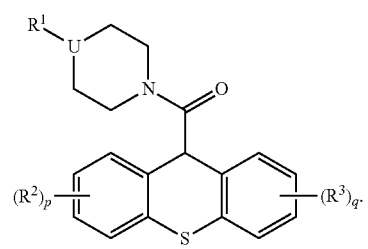

22. The method of claim 21, wherein said compound is:

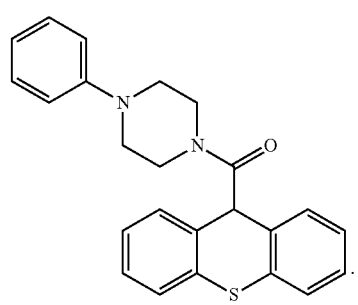

23. The method of claim 1, wherein said subject is a mammal.
24. The method of claim 23, wherein said mammal is a human.
25. The method of claim 1, wherein said lymphoma is a prostate cancer metastasis.
26. The method of claim 1, wherein said lymphoma is a pancreatic cancer metastasis.
27. The method of claim 1, wherein said lymphoma comprises cutaneous T-cell lymphoma (CTCL) or a metastasis thereof.
28. The method of claim 1, wherein said compound is administered in combination with at least one other agent effective at treating a lymphoma.
29. The method of claim 1, wherein said compound is formulated for parenteral administration, oral administration, rectal administration, intranasal administration, topical administration, administration by inhalation, or administration via a suppository.
30. The method of claim 29, wherein said parenteral administration is intravenous, subcutaneous, intraperitoneal, intraarterial, transdermal, or intramuscular administration.
31. The method of claim 1, wherein said compound is formulated for intravenous administration.

* * * * *